(12) United States Patent
Ralph et al.

(10) Patent No.: US 7,507,255 B2
(45) Date of Patent: **\*Mar. 24, 2009**

(54) INSERTION TOOL FOR USE WITH TRIAL INTERVERTEBRAL DISTRACTION SPACERS

(75) Inventors: James D. Ralph, Seaside Park, NJ (US); Stephen Tatar, Montville, NJ (US); Thomas J. Errico, Summit, NJ (US)

(73) Assignee: SpineCore, Inc., Summit, NJ (US)

( \* ) Notice: Subject to any disclaimer, the term of this patent is extended or adjusted under 35 U.S.C. 154(b) by 281 days.

This patent is subject to a terminal disclaimer.

(21) Appl. No.: 10/991,024

(22) Filed: Nov. 17, 2004

(65) Prior Publication Data

US 2005/0071011 A1    Mar. 31, 2005

Related U.S. Application Data

(63) Continuation of application No. 10/115,751, filed on Apr. 3, 2002, now Pat. No. 6,855,151, which is a continuation of application No. 09/906,120, filed on Jul. 16, 2001, now Pat. No. 6,428,544.

(51) Int. Cl.
  *A61F 2/44* (2006.01)
  *A61F 2/00* (2006.01)
(52) U.S. Cl. ............................ 623/17.16; 623/17.11
(58) Field of Classification Search .............. 606/90, 606/99, 61; 623/17.11–17.16
  See application file for complete search history.

(56) References Cited

U.S. PATENT DOCUMENTS

| | | | |
|---|---|---|---|
| 3,486,505 A | 12/1969 | Morrison | |
| 4,566,466 A | 1/1986 | Ripple et al. | |
| 4,927,425 A | 5/1990 | Lozier | |
| 5,236,460 A | 8/1993 | Barber | |
| 5,534,030 A | 7/1996 | Navarro et al. | |
| 5,562,447 A | 10/1996 | Moy et al. | |
| 5,683,464 A | 11/1997 | Wagner et al. | |
| 5,782,830 A | 7/1998 | Farris | |
| 5,910,141 A | 6/1999 | Morrison et al. | |
| 6,015,436 A | \* | 1/2000 | Schonhoffer .............. 623/17.16 |

(Continued)

OTHER PUBLICATIONS

Synthes. Surgical Technique Using FRA Spacer Instruments: Technique Guide. (1996).

(Continued)

*Primary Examiner*—Pedro Philogene
(74) *Attorney, Agent, or Firm*—Lerner, David, Littenberg, Krumholz & Mentlik, LLP

(57) ABSTRACT

A trial spacer kit has a plurality of trial spacers of varying heights. Each spacer includes a disc having a top surface and a bottom surface defining a height of said spacer, an annular groove formed in said disc that defines a central trunk of said spacer, the central trunk extending between the top and bottom surfaces of said spacer, a first radial flange provided at an upper end of the central trunk and a second radial flange provided at a lower end of the central trunk. The annular grooves of the spacers have a common dimension. The radial flanges of a first one of the spacers is thicker than the radial flanges of a second one of the spacers so that the first one of the spacers has a greater height than the second one of the spacers.

25 Claims, 13 Drawing Sheets

U.S. PATENT DOCUMENTS

| | | |
|---|---|---|
| 6,066,174 A | 5/2000 | Farris |
| 6,113,639 A | 9/2000 | Ray et al. |
| 6,174,311 B1 | 1/2001 | Branch et al. |
| 6,193,757 B1 | 2/2001 | Foley et al. |
| 6,319,257 B1 | 11/2001 | Carignan et al. |
| 6,402,785 B1 * | 6/2002 | Zdeblick et al. .......... 623/17.16 |
| 6,428,544 B1 | 8/2002 | Ralph et al. |
| 6,436,102 B1 | 8/2002 | Ralph et al. |
| 6,440,142 B1 | 8/2002 | Ralph et al. |
| 6,447,548 B1 | 9/2002 | Ralph et al. |
| 6,471,725 B1 | 10/2002 | Ralph et al. |
| 6,478,801 B1 | 11/2002 | Ralph et al. |
| 6,554,864 B2 | 4/2003 | Ralph et al. |
| 6,562,047 B2 * | 5/2003 | Ralph et al. ................... 606/99 |
| 6,607,559 B2 | 8/2003 | Ralph et al. |
| 6,623,525 B2 | 9/2003 | Ralph et al. |
| 6,660,038 B2 * | 12/2003 | Boyer et al. ............. 623/17.15 |
| 6,740,119 B2 | 5/2004 | Ralph et al. |
| 6,805,716 B2 * | 10/2004 | Ralph et al. .............. 623/17.16 |
| 6,837,904 B2 | 1/2005 | Ralph et al. |
| 6,863,689 B2 | 3/2005 | Ralph et al. |
| 6,890,356 B2 | 5/2005 | Ralph et al. |
| 7,153,310 B2 * | 12/2006 | Ralph et al. ................... 606/99 |
| 2002/0026242 A1 | 2/2002 | Boyle et al. |
| 2003/0014057 A1 | 1/2003 | Ralph et al. |
| 2003/0014109 A1 | 1/2003 | Ralph et al. |
| 2003/0014110 A1 | 1/2003 | Ralph et al. |
| 2003/0014113 A1 | 1/2003 | Ralph et al. |
| 2003/0014115 A1 | 1/2003 | Ralph et al. |
| 2003/0023245 A1 | 1/2003 | Ralph et al. |
| 2003/0023310 A1 | 1/2003 | Ralph et al. |
| 2003/0028252 A1 | 2/2003 | Ralph et al. |
| 2003/0195627 A1 | 10/2003 | Ralph et al. |
| 2004/0024407 A1 | 2/2004 | Ralph et al. |

OTHER PUBLICATIONS

Link, Surgical Technique, (1988).

* cited by examiner

Section A - A

Section A - A

Section B-B

Section A-A

Section B-B

Section A-A

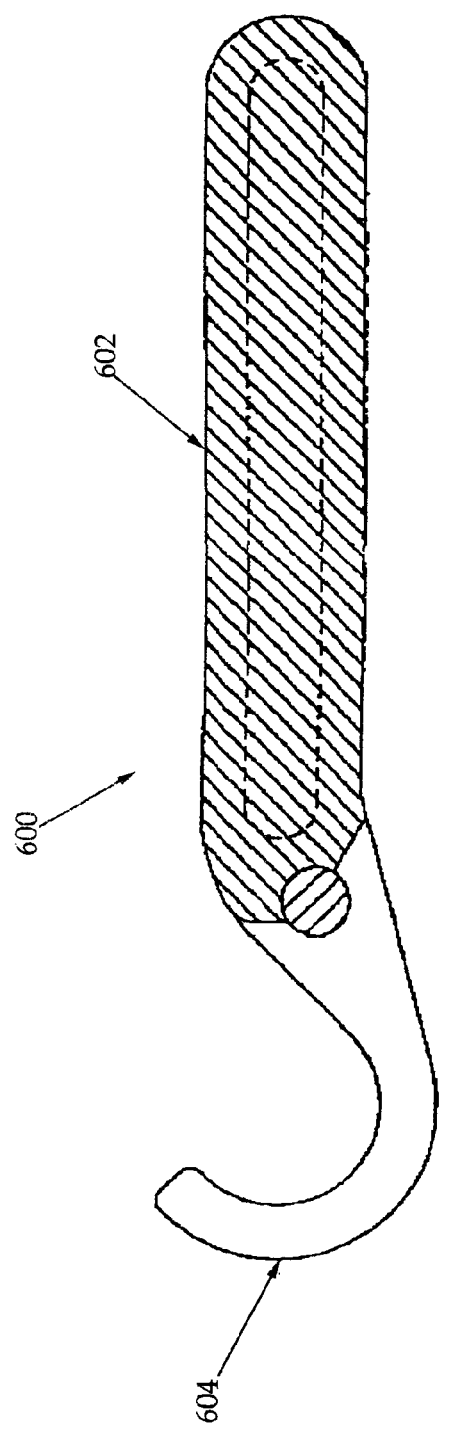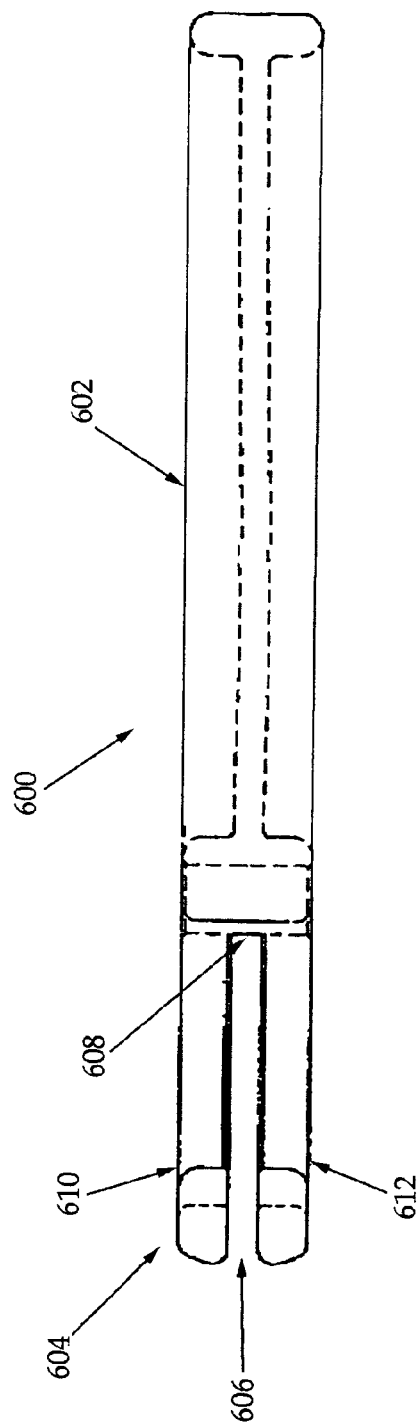
Fig. 6a
Fig. 6b

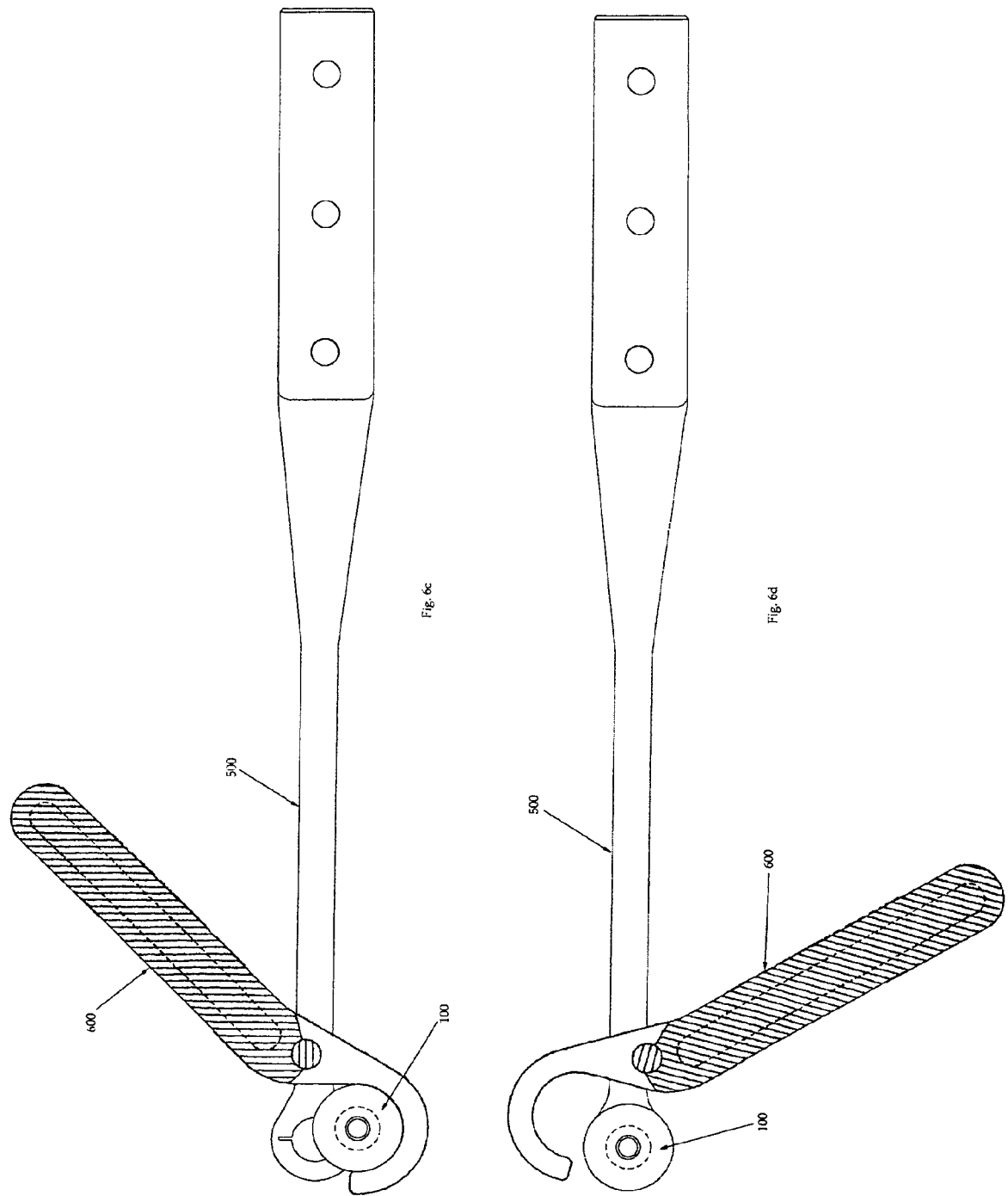

INSERTION TOOL FOR USE WITH TRIAL INTERVERTEBRAL DISTRACTION SPACERS

CROSS REFERENCE TO RELATED APPLICATIONS

The present application is a continuation of U.S. patent application Ser. No. 10/115,751, filed Apr. 3, 2002, now U.S. Pat. No. 6,855,151, which is a continuation of U.S. patent application Ser. No. 09/906,120, filed Jul. 16, 2001, now U.S. Pat. No. 6,428,544, the disclosures of which are hereby incorporated herein by reference.

BACKGROUND OF THE INVENTION

This invention relates generally to a treatment for scoliosis and more specifically to the instruments, implants, distracting trial spacers, and surgical methodology used in the treatment and correction of scoliosis. The bones and connective tissue of an adult human spinal column consists of more than 20 discrete bones. These more than 20 bones are anatomically categorized as being members of one of four classifications: cervical, thoracic, lumbar, or sacral. They are coupled sequentially to one another by tri-joint complexes that consist of an anterior intervertebral disc and the two posterior facet joints. The anterior intervertebral discs of adjacent bones are cushioning cartilage spacers.

The spinal column of bones is highly complex in that it includes these 20 bones coupled to one another (and others), and it houses and protects critical elements of the nervous system having innumerable peripheral nerves and circulatory bodies in close proximity. In spite of these complications, the spine is a highly flexible structure, capable of a high degree of curvature and twist in nearly every direction.

Genetic, congenital and/or developmental irregularities are the principle causes that can result in spinal pathologies in which the natural curvature of the spine lost. Scoliosis is a very common one of these types of irregularities, resulting in a sequential misalignment of the bones and intervertebral discs of the spine. Major causes of scoliosis are idiopathic (i.e., unknown cause), congenital developmental anomalies and neuromuscular disorders such as cerebral palsy. The misalignment usually manifests itself in an asymmetry of the vertebral bodies, such that, over a sequence of spinal bones, the spine twists and/or bends to one side. In severe cases, neurological impairment and/or physiological disability may result.

The present surgical technique for treating scoliosis (as well as other spinal conditions) includes the implantation of a plurality of hooks and/or screws into the spinal bones, connecting rods to these elements, physically bracing the bones into the desired positions, and permitting the bones to fuse across the entire assembly. This immobilization often requires anterior plates, rods and screws and posterior rods, hooks and/or screws. Alternatively, spacer elements are positioned between the sequential bones, which spacers are often designed to permit fusion of the bone into the matrix of the spacer from either end, hastening the necessary rigidity of the developing bone structure. Spacers allow bone fusion to grow into or around them. There are two classes of intervertebral spacers: horizontal cages such as the BAK.TM. and Ray cages, as described and set forth in exemplary U.S. Pat. No. 5,015,247 to Michelson and U.S. Pat. No. 5,026,373 to Ray et al., respectively, and vertical cages such the Harms cages, as described and set forth in exemplary U.S. Pat. No. 4,820,305.

Similar techniques have been employed in other spinal infirmities, including collapsed disc spaces (failure of the intervertebral disc), traumatic fractures, and other degenerative disorders. While the present invention has many applications, such applications include the treatment of any spinal disorder in which the space between vertebral bones needs to be surgically separated (the bones distracted), realigned and then fused to one another.

A variety of systems have been disclosed in the art which achieve immobilization and/or fusion of adjacent bones by implanting artificial assemblies in or on the spinal column. The region of the back that needs to be immobilized, as well as the individual variations in anatomy, determine the appropriate surgical protocol and implantation assembly. With respect to the failure of the intervertebral disc, and the insertion of implants and/or height restorative devices, several methods and devices have been disclosed in the prior art.

Restoring the appropriate height and orientation of the vertebral bones and the intervertebral space is the first step in the surgical strategy for correcting this condition. Once this is achieved, one class of surgical implantation procedures involves positioning a device into the intervening space. This may be done through a posterior approach, a lateral approach, or an anterior approach. Various implant devices for this purpose include femoral ring allograft, cylindrical metallic devices (i.e., cages), and metal mesh structures that may be filled with suitable bone graft materials. Some of these implant devices are only suitable for one direction of approach to the spine. All of these devices, however, are provided with the intention that the adjacent bones will, once restored to their appropriate alignment and separation, then grow together across the space and fuse together (or at least fuse into the device implanted between the bones).

Most recently, the development of non-fusion implant devices, which purport to permit continued natural movement in the tri-joint complex have provided great promise. The instrumentation and methods for the implantation of these non-fusion devices, as well as the implantation of the fusion devices catalogued previously, therefore should integrate the functions of restoring proper anatomical spacing and easy insertion of the selected device into the formed volume.

It is, therefore, an object of the present invention to provide a new and novel treatment for scoliosis, as well as for the treatment of spinal pathologies in general.

It is, correspondingly, another object of the present invention to provide an intervertebral distraction trial tool which more accurately and easily separates collapsed intervertebral spaces.

It is further an object of the present invention to provide an intervertebral distraction trial tool which more can be used to correct scoliosis and/or restore normal alignment to the spine.

It is further an object of the present invention to provide an instrument that proficiently and simply manages the insertion, rotation, and removal of the intervertebral distraction trial tools.

It is further an object of the present invention to provide an implantable spacer device that permits more anatomically appropriate and rapidly osteogenic fusion across the intervertebral space.

Other objects of the present invention not explicitly stated will be set forth and will be more clearly understood in conjunction with the descriptions of the preferred embodiments disclosed hereafter.

SUMMARY OF THE INVENTION

The present invention is directed to a method of treatment of scoliosis and other spinal disorders. This method of treatment further includes several new and novel instruments, implantable trial distraction elements, and intervertebral spacer implants. Inasmuch as the description of the new and novel method cannot be complete without a description of each of these integral members, the following includes ample explanation of these elements as well as description of the surgical techniques.

First, the patient spine is exposed through an anterior approach (i.e., the surgeon creates an access hole which permits direct interaction with the anterior and/or anterio-lateral portion of the intervertebral bodies). In the case of scoliosis, as well as in other disorders in which the intervertebral space requires distraction and/or repositioning, the surgeon removes the intervertebral disc material, usually leaving some portion of the annulus (the cylindrical weave of fibrous tissue which normally surrounds and constrains the softer cartilage cushion of the disc material). The surgeon then, in succession, inserts a series of intervertebral trial spacers of defined width. Each of the series of spacers is of a progressively wider thickness, resulting in the continual widening of the space until restoration of the proper disc height has been achieved. Proper disc height restoration is determined by surgical experience, and by observation of the annulus. (Often, the tightening of the annulus indicates that the proper disc height has been reached, inasmuch as the annulus is much less likely to be distorted by the same disruption that caused the intervertebral disc to collapse in the first place.)

More particularly, with respect to the specific instruments disclosed herein, a series of solid trial spacer elements and an instrument for their insertion and removal is now provided. Each trial spacer is a generally cylindrical disc having a deep annular groove at its midpoint, which forms a central trunk and radial flanges at each end of the trunk. Stated alternatively, two cylindrical upper and lower halves of the disc are held in a closely coaxial spaced apart association by the central trunk, which forms a coaxial bridge between the upper and lower halves. The annular groove is particularly useful for holding the spacer using the spacer insertion instrument of the invention, described below, in that the holding end of the insertion instrument fits within the groove.

A variety of features of embodiments of the trial spacer elements are disclosed. In some embodiments, such as the first and second embodiments described below, support portions (the portions that are in contact with the adjacent vertebral bodies when the spacer is disposed between the bodies) of the top and bottom surfaces are parallel. Spacers having this feature are generally described herein as "constant thickness" trial spacers. In other embodiments, such as the third and fourth embodiments described below, the support portions are not parallel, providing an overall taper to the spacer at an angle. Spacers having this feature are generally described herein as "tapered thickness" trial spacers. The tapered thickness trial spacers are particularly useful for treating scoliosis, as described below.

Other features of embodiments of the trial spacer elements include beveled flanges and non-parallel annular groove walls. More specifically, in some embodiments, such as the second and fourth embodiments described below, the flanges are radially beveled in that an outer edge of the top surface of the disc is tapered toward an outer edge of the bottom surface of the disc. In other embodiments, such as the first and third embodiments described below, the flanges are not radially beveled in this manner. The radial beveling feature can be particularly useful for easing the insertion of the spacer in between collapsed vertebral bodies, as described below. Further, in some embodiments, such as the first and third embodiments described below, the walls of the annular groove are parallel, such that the floor of the groove is as wide as the opening of the groove. In other embodiments, such as the second and fourth embodiments described below, the walls of the annular groove are tapered toward one another with the increasing depth of the groove, such that the floor of the groove is narrower than the opening of the groove. Each type of annular groove is useful, depending on the particular surgical application and on the particular embodiment of the spacer insertion instrument that is used to insert the spacer.

Collections of trial spacer elements are provided by the invention. Preferably, each spacer in a particular set maintains the same diameter as the other spacers in the set. (It shall be understood that different collections of spacers may be provided such that the diameter of the selected collection of trial spacers is appropriate for the specific patient being treated.) Also preferably, each spacer in a particular set has a predetermined depth that differs from the depth of the other spacers in the set. The predetermined depth is provided in that while each spacer in the set shares the same annular groove dimensions (so that each can be held by the same insertion instrument), each spacer has a different flange thickness (in sets where the spacers are constant thickness spacers). For sets of tapered thickness spacers, the predetermined maximum depth and predetermined minimum depth (the two depths providing the overall taper) are provided in that while each spacer in the set shares the same annular groove dimensions (so that each can be held by the same insertion instrument), each spacer has a different maximum flange thickness and a different minimum flange thickness. Preferably in sets of tapered thickness spacers, the overall taper angle is the same for each spacer in the set. The usefulness of providing sets of spacers similar in most respects except for the depth dimension will be described in greater detail below.

With regard to the instrument for the insertion and removal of the trial spacer elements, a first embodiment (particularly useful for inserting constant thickness trial spacers) of a spacer insertion tool includes an elongated shaft and a handle at one end of the shaft. The distal end of the shaft includes semi-circular hook that is adapted to hold a trial spacer within an enclosure formed by the hook. The angle swept out by the hook is slightly greater than 180 degrees, but the inner diameter of the hook is only slightly larger than the central trunk of the trial spacer. Therefore, the trial spacer may be snapped into the enclosure, but maintains complete rotational freedom within its grasp. A loading tool may be provided to assist in the loading and unloading of the trial spacer from the trial spacer insertion instrument of this embodiment. This loading tool comprises a forked hook having two curved tines separated by a notch that engages the shaft of the insertion tool as the tines engage the flanges of the trial spacer, to force the trial spacer into the enclosure. Alternatively and/or additionally, the same device may be utilized to remove the spacer from the enclosure, by reversing the position of the forked hook relative to the insertion tool and the spacer.

The insertion tool of this embodiment can be used to insert a series of constant thickness trial spacers (some of which may have beveled flange edges for easing the insertion between the collapsed bones and into the space to be distracted). More specifically, thinner trial spacers can initially be inserted into the spacer, followed successively by thicker trial spacers until the desired spacing is achieved. Once the appropriate spacing has been achieved, immobilization of the spine by fixation, fusion, or non-fusion techniques and devices, such as those set forth in co-pending U.S. patent application Ser. Nos. 09/906,117 and 09/906,118, entitled "An Intervertebral Spacer Device Having a Wave Washer Force Restoring Element" and "An Intervertebral Spacer Device Having a Spiral Wave Washer Force Restoring Element", respectively, as well as U.S. Pat. No. 5,989,291, entitled "An Intervertebral Spacer Device", each of which has been assigned to the same assignee as the present invention, the specifications of which are all fully incorporated herein by reference, may be desirable.

While simple distraction to a constant height across the intervertebral space is appropriate for standard disc compression pathologies, in the case of scoliosis, simple constant thickness distraction is insufficient to remediate the pathological condition. What is necessary is the distraction of the sequence of spaces, each to an appropriate angle and height, such that the overall spinal configuration is anatomically correct. Tapered trial spacers, such as those disclosed in the present application, are the first such distraction tools to provide such a tailored correction of the misangulation of the spinal bones.

More particularly, the surgeon inserts the tapered trial spacers into the intervertebral space (presumably from the anterior, or anterio-lateral, approach) with the narrow edge of the trial spacer forming a wedge and sliding between the adjacent bones. By utilizing either a second or third embodiment of the spacer insertion tool, described more fully below, the surgeon may turn the spacer around its axis within the intervertebral space to find the most appropriate rotational position (corresponding to the most desirable straightening effect on the spinal column). Stated alternatively, each of the tapered trial spacers has an overall wedge shape that generally corresponds to the pathological tapering of the adjacent bones that characterizes scoliosis. By rotating the wedge-shaped spacer after it has been placed between the adjacent bones, the overall disc alignment may be compensated, restoring appropriate anatomical status. It should be understood that additional rotation of the spacer may restore lordosis to the spine, and that over-rotation (if the particular spine is flexible enough) of the spacer would result in a pathological curvature in the opposite direction.

This second embodiment of the spacer insertion tool includes a handle and an elongated dual shaft, the dual shaft culminating in a trial spacer grasping pincer, rather than the simple hook of the first embodiment. This pincer differs from the hook of the first embodiment of the trial spacer insertion tool described above, inasmuch as the dual shaft includes a fixed shaft and a selectively engagable shaft which, together, form pincer. More specifically, the fixed shaft includes a semicircular hook portion of the pincer at its distal end, having an enclosure within which a trial spacer can be placed. The selectively engagable shaft includes the complementary portion of the pincer, which moves toward the hook portion to grasp and hold the trial spacer when the engagable shaft is engaged, and moves away from the hook portion to release the trial spacer when the engagable shaft is disengaged. (The spacer can be unloaded and loaded when the engagable shaft is disengaged.) The engagement action prevents the spacer from moving relative to the tool, and therefore permits the surgeon to rotate the tapered spacer in between the vertebral bodies (by contrast, the first embodiment of the trial spacer insertion instrument permitted the spacer to rotate freely in the enclosure of the hook). There are alternative insertion and rotating instruments that may be designed, so long as they selectively and alternatingly release or hold the trial spacer securely against rotation (the spacer cannot be permitted to rotate freely if it must be turned in the intervertebral space). The tapered trial spacers themselves can include angle markers that clearly indicate to the surgeon the amount of rotation that was necessary for the correction of the spinal deformity. Such angle markers can also serve as a guide for the implantation of a secondary bone graft (e.g., a femoral ring) or another intervertebral spacer device.

Once the surgeon has determined the appropriate geometry for the surgical implants via the trial spacers, he or she is ready to immobilize the spine in that position. While multiple ways for immobilizing the spine are disclosed in the prior art, any one of which and others may be suitable for the specific surgical patient's treatment, three alternative ways are herein described.

First, the trial spacers may be left in the patient while rod fixation apparatuses (anterior or posterior) are mounted to the spine, thereby holding the spine in its desired orientation even after the trial spacers are subsequently removed. Alternatively, surface plating and/or intervertebral cage devices may be mounted to the spine to promote fusion without the need for bulky rod assemblies. (While this approach may seem more surgically desirable, questions regarding the long term stability of these constructs have led some surgeons to chose combinations of rodding and cages.)

A third approach to immobilizing the corrected spine is to insert a shaped bone graft, or suitably contoured porous metal spacer, into the properly distracted intervertebral space is described more fully in co-pending U.S. patent application Ser. Nos. 09/844,904 and 09/906,123, respectively entitled "A Porous Interbody Fusion Device Having Integrated Polyaxial Locking Interference Screws" and "Porous Intervertebral Distraction Spacers", assigned to the same assignee as the present invention, the specifications of each being fully incorporated herein by reference.

The tapered trial spacers may also serve as precursors (measuring instruments) for another spacer (e.g., a porous metal spacer), similarly shaped, which is inserted into the intervertebral space by the same instrument.

Therefore, the present invention, in its many embodiments and components, is directed to a surgical treatment for restoring a proper anatomical spacing and alignment to vertebral bones of a scoliosis patient. In one desired embodiment, the present invention comprises a surgical method, which in a first embodiment, comprises: 1. determining an angular misalignment associated with at least one pair of adjacent vertebral bones; 2. sequentially inserting and removing a series of progressively wider cylindrical spacer elements into the corresponding intervertebral space between said at least one pair of adjacent vertebral bones until the proper anatomical spacing between the pair of adjacent vertebral bones is restored; 3. for each intervertebral space, inserting a diametrically tapered cylindrical spacer element into the intervertebral space between said corresponding pair of adjacent vertebral bones; and 4. rotating said diametrically tapered cylindrical spacer element such that the rotational orientation of the tapered cylindrical spacer element introduces the appropriate counter offset to the intervertebral space of the previously misaligned scoliotic vertebral bones, thereby restoring the proper anatomical alignment of the vertebral bones.

It shall be understood that each of said progressively wider cylindrical spacer elements includes substantially parallel upper and lower surfaces. The method may also include the additional step of affixing immobilizing instrumentation to the vertebral bones of the patient to hold the restored vertebral bones rigidly in position to facilitate fusion, and positioning bone fusion material adjacent to the restored vertebral bones. It shall be understood that other equivalent (or alternatively efficacious) means for facilitating healing, such as including positioning a non-fusion intervertebral spacer device between the restored vertebral bones so that a proper anatomical motion may be possible.

The surgical treatment set forth above should be further refined inasmuch with respect to the diametrically tapered cylindrical spacer elements, such that each has a width along its central cylindrical axis substantially equivalent to the axial width of the final cylindrical spacer element utilized in the step of sequentially inserting and removing the series of progressively wider cylindrical spacer elements to restore the proper anatomical spacing between the pair of adjacent vertebral bones.

It shall be understood that each progressively wider cylindrical spacer element and/or diametrically tapered cylindrical spacer element may comprise solid or porous metal, or a porous or non-porous organic implantable material.

For clarity, this embodiment of the surgical method includes exposing an intervertebral space between adjacent vertebral bones, distracting the space by sequentially inserting therein and subsequently removing therefrom a plurality of intervertebral spacers, each having a predetermined thickness, the thicknesses incrementally increasing from one spacer to another at an increment acceptable for safely distracting the space to a desired distance, and when adjustment of an angular misalignment of the adjacent vertebral bones is necessary, inserting, and when necessary rotating, in the intervertebral space, at least one diametrically tapered intervertebral spacer having a thickness along its central cylindrical axis sufficient to maintain the desired distance between the adjacent vertebral bones, and a diametrical angle sufficient to reorient the adjacent bones to the desired configuration, when rotational adjustment of the angular misalignment is necessary, rotating said tapered intervertebral spacer within the space until the desired alignment is established.

In an alternative embodiment, in which porous spacers are utilized, the surgical method of the present invention may comprise: determining an angular misalignment associated with at least one pair of adjacent vertebral bones; sequentially inserting and removing a series of progressively wider cylindrical spacer elements into the corresponding intervertebral space between said at least one pair of adjacent vertebral bones until the proper anatomical spacing between the pair of adjacent vertebral bones is restored; for each intervertebral space, inserting a diametrically tapered cylindrical porous spacer element into the intervertebral space between said corresponding pair of adjacent vertebral bones; rotating said diametrically tapered cylindrical porous spacer element such that the rotational orientation of the tapered cylindrical porous spacer element introduces the appropriate counter offset to the intervertebral space of the previously misaligned scoliotic vertebral bones, thereby restoring the proper anatomical alignment of the vertebral bones; and stabilizing the pair of adjacent vertebral bones to permit infused growth of bone into the diametrically tapered cylindrical porous spacer element.

As shall be readily understood, in its most basic form, the method of the present invention principally consists of sequentially inserting and removing a series of progressively wider cylindrical spacer elements into the intervertebral space between adjacent vertebral bones until the distance between the vertebral bones is anatomically appropriate.

More particularly, with respect to the various spacers of the present invention, in its most basic form, the spacers comprise a plurality of sequentially axially wider disc spacer elements, the sequential insertion and removal of which, into an intervertebral space effects a widening of the intervertebral space, such that a desired anatomical spacing of adjacent vertebral bones may be restored. These spacers may include beveled upper and lower circumferential radial edges which facilitate the application of the desired spreading force to the adjacent vertebral bones. For the ease of surgical use, these spacers may each include an engagement locus which couples with a corresponding insertion and removal tool to facilitate the same. This locus comprises an axially medial groove into which said insertion and removal tool can be seated. In two alternative embodiments, the medial groove may comprises a constant width, such that each disc spacer element may rotate freely within the corresponding insertion and removal tool. Alternatively, the groove may be a radially widening groove, such that each disc spacer element may be prevented from rotating freely with respect to the corresponding insertion and removal tool by a clamping action thereof, thereby permitting the controlled rotation of the corresponding disc spacer element within the intervertebral space by manipulation of the insertion and removal tool.

Tapered spacers, for use in reorienting as well as distracting the alignment of the adjacent vertebral bones may be used. These tapered spacers comprise diametrically tapered upper and lower surfaces. Ideally, for surgeon measurement purposes, each of the disc spacer elements includes at least two relative angle designation marks on at least one of said upper and lower surfaces such that a surgeon user may readily visually determine the rotational angle of said disc spacer element relative to a known reference.

It shall be understood that the intervertebral spacers each have a unique axial thickness, the thicknesses increasing sequentially from one spacer to another, the increasing thicknesses increasing incrementally, said plurality of spacers being particularly useful for gradually distracting adjacent vertebral bones in an anatomically appropriate manner.

A critical feature of the present invention is the potential for using porous spacers to distract and potentially reorient the spine, and that the spacers may be implanted permanently into the space between the vertebral bones such that bone ingrowth and solid fusion may occur across the intervertebral space.

As introduced above, insertion tools are additional components of the present invention. In a first embodiment, the instrument for inserting and removing an intervertebral spacer into and out from an intervertebral space between adjacent vertebral bones, the spacer having a trunk portion having a longitudinal axis and flange portions at each longitudinal end of the trunk, the instrument comprises: a shaft having a proximal end and a distal end; said proximal end including a handle; and a holding structure provided at the distal end, which holding structure includes an enclosure within which the trunk of the spacer may be selectively introduced and maintained therein, the holding structure having an opening leading to the enclosure and through which opening the trunk of the spacer may be selectively passed to when forced therethough. More specifically, the trunk of the spacer has a first width, the opening has a second width which is incrementally smaller than the first width, and the enclosure has a third width which accommodates the first width, such that selective introduction of the trunk through the opening and into the enclosure requires a force to elastically widen the opening such that the trunk may pass through the opening and into the enclosure, the restoration of the opening providing an occlusion which maintains the trunk within the enclosure. As suggested above, the trunk is generally cylindrical and, therefore, the holding structure includes a hook having a curvate extent which forms a partial-circular enclosure, and which curvate extent fits between the flanges when the trunk is maintained within the enclosure.

In such an embodiment, the intervertebral spacer is selectively snapped into and out of the enclosure through the opening, and such that the intervertebral spacer may be rotationally freely held within the enclosure. In order to snap the spacer into and out of the enclosure, a second element is often utilized. This second helper tool comprises a handle portion at one end, and a bifurcated pair of spaced apart curvate hook-shaped tines at the other. The tines have a radius of curvature greater than that of each of the spacers, such that when the first and second elements engage one another (at a fulcrum point at the point of bifurcation of the spaced apart curvate hook-shaped tines and a point between the handle and enclosure ends of the first element), the introduction and removal of the distraction member from the enclosure is facilitated.

In a second embodiment, which is more suited for the insertion, rotation and removal of the tapered spacers, the tool comprises a shaft having a proximal end and a distal end, said proximal end forming a handle and the distal end forming a spacer member engaging subassembly; said spacer member engaging subassembly including at least one selectively expanding and contracting enclosure into which the central core may be introduced when the engaging subassembly is in the expanded state, and which holds the spacer member so that it cannot move when the selectively expanding and contracting enclosure is rendered into the contracted state; and an actuating mechanism, extending from the proximal end to the distal end, by which the spacer member engaging subassembly may be selectively expanded and contracted. More specifically, the spacer member engaging subassembly comprises a fixed curvate hook defining a portion of the enclosure, a second, selectively advanceable and retractable, portion adjacent the fixed hook portion and said first and second portions forming said selectively expanding and contracting enclosure. Stated alternatively, the selectively expanding and contracting enclosure is formed by at least two members which are maintained in selectively slideable association with each other, at least one of said at least two members including a tapered edge thereof.

The instrument of this embodiment includes an actuating mechanism including a trigger element disposed in the handle portion, which trigger is actionably coupled to advancing and retracting cams which are coupled to the second portion to advance and retract the second portion in accordance with selective manipulation of the trigger. In more detail, the spacer member engaging subassembly comprises a fixed member and a selectively moveable member which, together, form said selectively expanding and contracting enclosure, and wherein said actuating mechanism comprises a trigger which is mechanically coupled to said selectively moveable member, the mechanical coupling including a rod, a plate having a protrusion, and a lever having a slot, the rod being connected at one end to the selectively moveable member and at another end to the plate, the protrusion engaging the slot, the lever being attached to the trigger, so that when the trigger is engaged, the lever pulls the plate protrusion by the slot, the plate pulls the rod, and the rod moves the selectively moveable member toward the fixed member.

In a third embodiment, the tool comprises a shaft having a proximal end forming a handle, and a distal end forming a claw subassembly for holding said spacer, said claw subassembly including a first pincer which is fixed at the distal end of the shaft and a second pincer which is selectively rotateable into and out of spacer holding association with said first pincer to hold and release, respectively, the spacer; and an actuation mechanism for selectively rotating the second pincer. The second pincer is rotateably mounted to the shaft and is spring biased away from the first pincer.

In this embodiment the actuation mechanism comprises a sliding member mounted to the shaft which is selectively moveable in the distal direction by a force sufficient to overcome the bias of the spring, the distally directed movement of the sliding member thereby causing the second pincer to move toward the fixed first pincer, and the subsequent retraction of the sliding member in a proximal direction causes the sliding member to disengage the second pincer and the permits the pincers to separate under the bias of the spring. In order to facilitate this action, the second pincer includes a tapered surface which is engaged by a corresponding surface of the sliding member, said engagement causes the second pincer to rotate relative to the first pincer.

More specifically, the intervertebral spacer comprises a cylindrical member having an annular groove defining a central axial core portion and a pair of flange portions at opposing ends thereof; and the claw subassembly engages the spacer at the central axial core.

Stated alternatively, this third embodiment comprises a pair of pincers, a first of this pair being fixed, and a second being coupled to the first in open-biased opposition thereto, and a sliding element which may be selectively translated into and out of engagement with said second pincer to close and open the pair of pincers, respectively. The pair of pincers define an intervertebral spacer grasping enclosure having an access opening through which the intervertebral spacer can be passed for placement into the enclosure when the sliding element is out of engagement with the second pincer, and the spacer is securely maintained between the first and second pincers when the sliding element has been translated into engagement with the second pincer. Ideally, the first and second pincers are mounted at the distal end of a common shaft, and the sliding element is translateable along said shaft; and wherein the second pincer has a portion thereof which is engaged by the sliding element to close the pair of pincers. In addition, the second pincer is mounted to the common shaft by a pivot joint, and the portion of the second pincer which is engaged by the sliding element is a tapered surface, the angle of which tapered surface, when engaged by the sliding element, causes the second pincer to rotate about the pivot joint, closing the first and second pincers.

BRIEF DESCRIPTION OF THE DRAWINGS

FIGS. 6a-b illustrates an embodiment of a loading accessory for a spacer insertion tool of the invention in side and top views, respectively.

FIG. 6c shows the loading accessory of FIGS. 6a-b in operation to load the spacer of FIG. 1a-c into the spacer insertion tool of FIG. 5a.

FIG. 6d shows the loading accessory of FIGS. 6a-b in operation to unload the spacer the spacer insertion tool of FIG. 5a.

DETAILED DESCRIPTION OF THE INVENTION

Figure 1A:
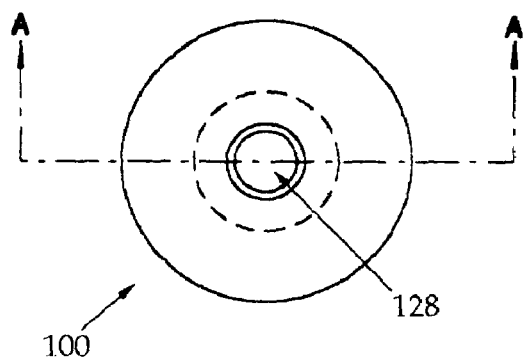
FIGS. 1a-c illustrates a first embodiment of an intervertebral trial spacer of the invention is illustrated in side, top and side cutaway views, respectively.

While the present invention will be described more fully hereinafter with reference to the accompanying drawings, in which particular embodiments and methods of implantation are shown, it is to be understood at the outset that persons skilled in the art may modify the invention herein described while achieving the functions and results of this invention. Accordingly, the descriptions which follow are to be understood as illustrative and exemplary of specific structures, aspects and features within the broad scope of the present invention and not as limiting of such broad scope. Like numbers refer to similar features of like elements throughout.

First, the patient spine is exposed through an anterior approach (i.e. the surgeon creates an access hole which permits direct interaction with the anterior and/or anterio-lateral portion of the intervertebral bodies). In the case of scoliosis, as well as in other disorders in which the intervertebral space requires distraction and/or repositioning, the surgeon removes the intervertebral disc material, usually leaving some portion of the annulus (the cylindrical weave of fibrous tissue which normally surrounds and constrains the softer cartilage cushion of the disc material). The surgeon then, in succession, inserts a series of intervertebral trial spacers of defined width. Each of the series of spacers is of a progressively wider thickness, resulting in the continual widening of the space until restoration of the proper disc height has been achieved. Proper disc height restoration is determined by surgical experience, and by observation of the annulus. (Often, the tightening of the annulus indicates that the proper disc height has been reached, inasmuch as the annulus is much less likely to be distorted by the same disruption that caused the intervertebral disc to collapse in the first place.)

More particularly, with respect to the specific instruments disclosed herein, a series of solid trial spacer elements and an instrument for their insertion and removal is now provided. Each trial spacer is a generally cylindrical disc having a deep annular groove at its midpoint, which forms a central trunk and radial flanges at each end of the trunk. Stated alternatively, two cylindrical upper and lower halves of the disc are held in a closely coaxial spaced apart association by the central trunk, which forms a coaxial bridge between the upper and lower halves. The annular groove is particularly useful for holding the spacer using the spacer insertion instrument of the invention, described below, in that the holding end of the insertion instrument fits within the groove.

A variety of features of embodiments of the trial spacer elements are disclosed. In some embodiments, such as the first and second embodiments described below, support portions (the portions that are in contact with the adjacent vertebral bodies when the spacer is disposed between the bodies) of the top and bottom surfaces are parallel. Spacers having this feature are generally described herein as "constant thickness" trial spacers. In other embodiments, such as the third and fourth embodiments described below, the support portions are not parallel, providing an overall taper to the spacer at an angle. Spacers having this feature are generally described herein as "tapered thickness" trial spacers. The tapered thickness trial spacers are particularly useful for treating scoliosis, as described below.

Other features of embodiments of the trial spacer elements include beveled flanges and non-parallel annular groove walls. More specifically, in some embodiments, such as the second and fourth embodiments described below, the flanges are radially beveled in that an outer edge of the top surface of the disc is tapered toward an outer edge of the bottom surface of the disc. In other embodiments, such as the first and third embodiments described below, the flanges are not radially beveled in this manner. The radial beveling feature can be particularly useful for easing the insertion of the spacer in between collapsed vertebral bodies, as described below. Further, in some embodiments, such as the first and third embodiments described below, the walls of the annular groove are parallel, such that the floor of the groove is as wide as the opening of the groove. In other embodiments, such as the second and fourth embodiments described below, the walls of the annular groove are tapered toward one another with the increasing depth of the groove, such that the floor of the groove is narrower than the opening of the groove. Each type of annular groove is useful, depending on the particular surgical application and on the particular embodiment of the spacer insertion instrument that is used to insert the spacer.

Collections of trial spacer elements are provided by the invention. Preferably, each spacer in a particular set maintains the same diameter as the other spacers in the set. (It shall be understood that different collections of spacers may be provided such that the diameter of the selected collection of trial spacers is appropriate for the specific patient being treated. For example, the diameters of the trial spacers in a collection that is suitable for use with pediatric patients would be smaller than the diameters of the trial spacers in a collection that is suitable for use with adult patients.) Also preferably, each spacer in a particular set has a predetermined depth that differs from the depth of the other spacers in the set. The predetermined depth is provided in that while each spacer in the set shares the same annular groove dimensions (so that each can be held by the same insertion instrument), each spacer has a different flange thickness (in sets where the spacers are constant thickness spacers). For sets of tapered thickness spacers, the predetermined maximum depth and predetermined minimum depth (the two depths providing the overall taper) are provided in that while each spacer in the set shares the same annular groove dimensions (so that each can be held by the same insertion instrument), each spacer has a different maximum flange thickness and a different minimum flange thickness. Preferably in sets of tapered thickness spacers, the overall taper angle is the same for each spacer in the set. The usefulness of providing sets of spacers similar in most respects except for the depth dimension will be described in greater detail below.

Figure 1B:
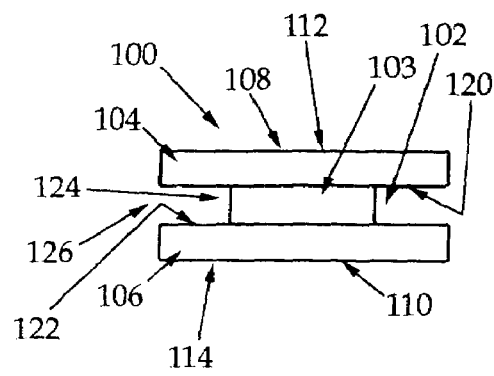
Figure 1C:
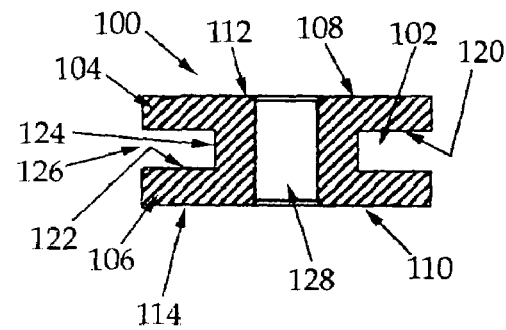

Referring now to FIGS. 1a-c, a first embodiment of an intervertebral trial spacer 100 of the invention is illustrated in side, top and side cutaway views, respectively. The spacer 100 is a cylindrical disc with an annular groove 102 that forms a central trunk 103 and radial flanges 104, 106 at each end of the trunk 102. In this embodiment, support portions 108,110 of the top and bottom surfaces 112,114 of the disc are parallel. Further in this embodiment, the walls 120,122 of the annular groove 102 are parallel, such that the floor 124 of the groove 102 is as wide as the opening 126 of the groove 102. Further in this embodiment, the spacer 100 has a central bore 128.

Figure 1D:
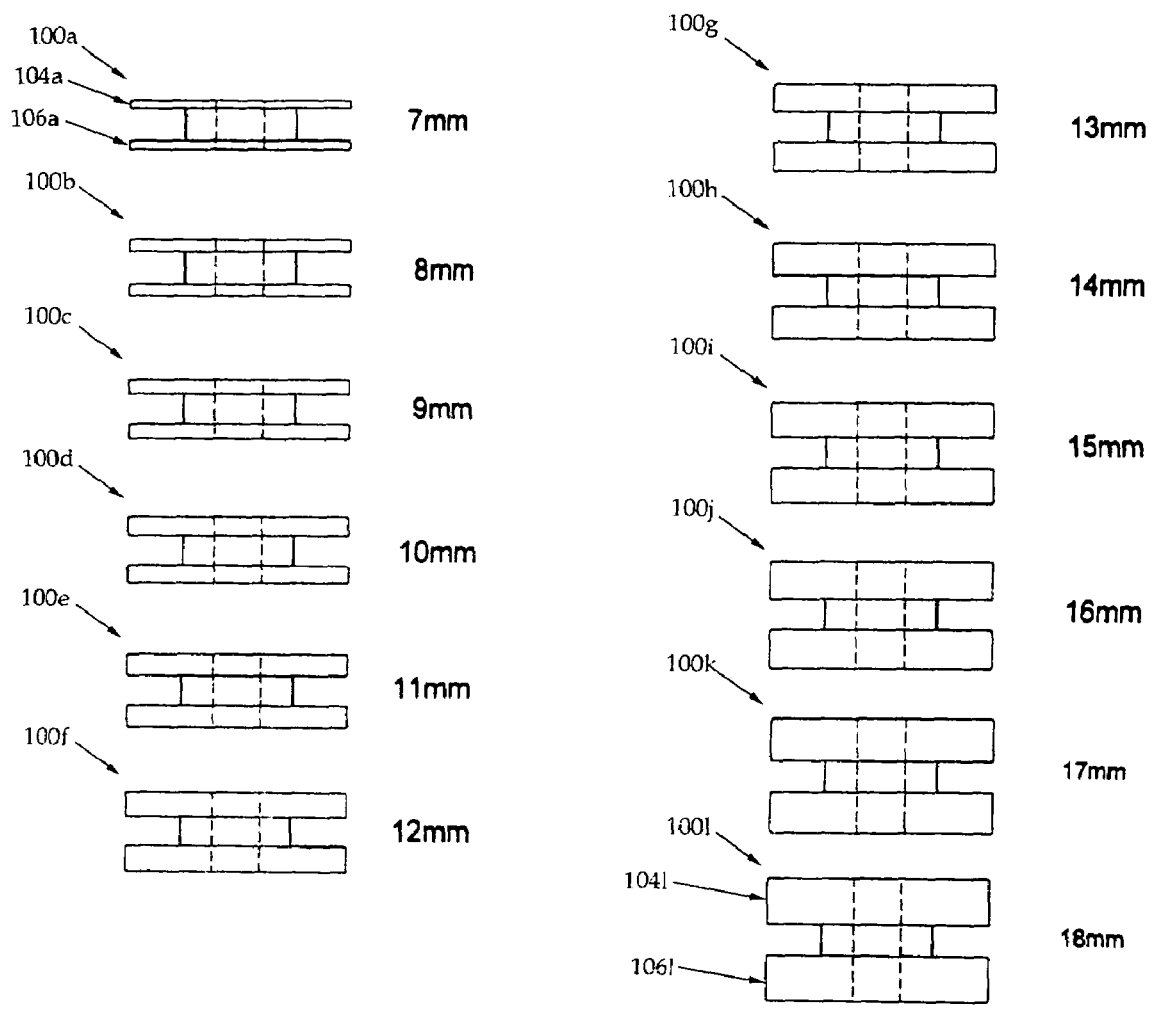
FIG. 1d illustrates a first set of intervertebral spacers of the invention in a side view.

Referring now to FIG. 1d, a set of intervertebral spacers 100a-l of the invention are illustrated in a side view. Each spacer 100a-l is formed generally similarly to the intervertebral spacer 100 of FIGS. 1a-c, except that each spacer 100a-l has a predetermined depth (denoted by the preferred dimension identified adjacent each spacer) provided in that while each spacer 100a-l shares the same annular groove dimensions as the other spacers, each spacer 100a-l has a different flange thickness dimension. For example, the flanges 104l, 106l are thicker than the flanges 104a,106a.

Figure 2A:
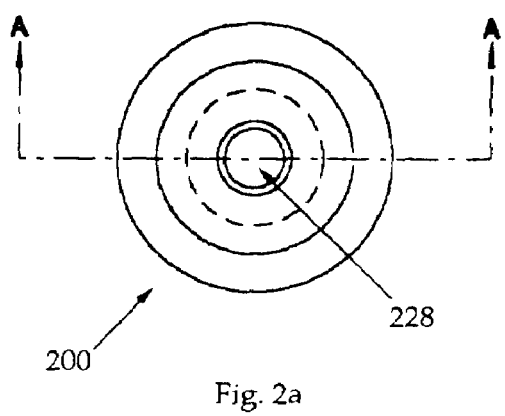
FIGS. 2a-c illustrate a second embodiment of an intervertebral spacer of the invention in side, top and side cutaway views, respectively.
Figure 2B:
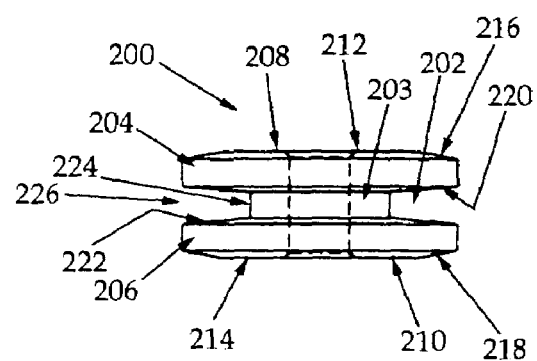
Figure 2C:
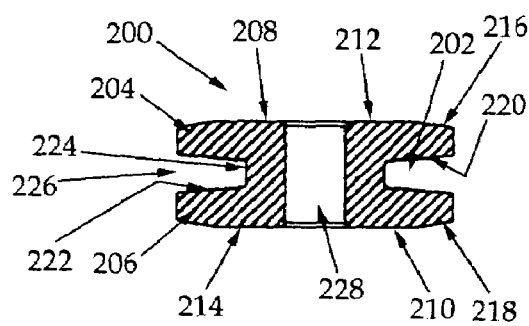

Referring now to FIGS. 2a-c, a second embodiment of an intervertebral spacer 200 of the invention is illustrated in side, top and side cutaway views, respectively. Similarly to the spacer 100, the spacer 200 is a cylindrical disc with an annular groove 202 that forms a central trunk 203 and radial flanges 204,206 at each end of the trunk 202. However, in this embodiment, the flanges 204,206 are radially tapered in that support portions 208,210 of the top and bottom surfaces 212, 214 of the disc are parallel, while an outer edge 216 of the top surface 212 is tapered toward an outer edge 218 of the bottom surface 214. Further in this embodiment, in contrast to the spacer 100, the walls 220,222 of the annular groove 202 are tapered toward one another with the increasing depth of the groove 202, such that the floor 224 of the groove 202 is more narrow than the opening 226 of the groove. Further in this embodiment, the spacer 200 has a central bore 228.

Figure 2D:
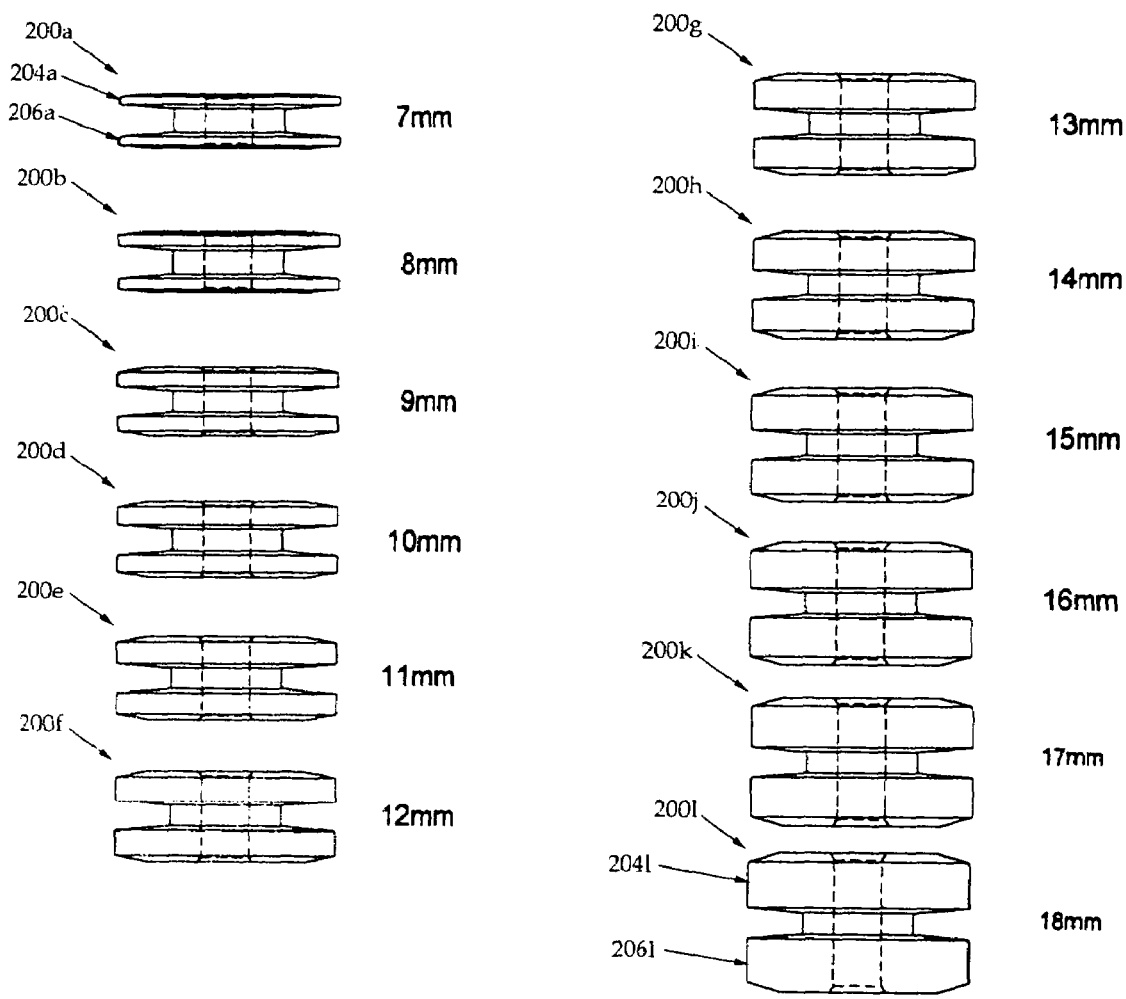
FIG. 2d illustrates a second set of intervertebral spacers of the invention in a side view.

Referring now to FIG. 2d, a set of intervertebral spacers 200a-l of the invention are illustrated in a side view. Each spacer 200a-l is formed generally similarly to the intervertebral spacer 200 of FIGS. 2a-c, except that each spacer 200a-l has a predetermined depth (denoted by the preferred dimension identified adjacent each spacer) provided in that while each spacer 200a-l shares the same annular groove dimensions as the other spacers, each spacer 200a-l has a different flange thickness dimension. For example, the flanges 204l, 206l are thicker than the flanges 204a,206a.

With regard to the instrument for the insertion and removal of the trial spacer elements, a first embodiment (particularly useful for inserting constant thickness trial spacers) of a spacer insertion tool includes an elongated shaft and a handle at one end of the shaft. The distal end of the shaft includes semi-circular hook that is adapted to hold a trial spacer within an enclosure formed by the hook. The angle swept out by the hook is slightly greater than 180 degrees, but the inner diameter of the hook is only slightly larger than the central trunk of the trial spacer. Therefore, the trial spacer may be snapped into the enclosure, but maintains complete rotational freedom within its grasp. A loading tool may be provided to assist in the loading and unloading of the trial spacer from the trial spacer insertion instrument of this embodiment. This loading tool comprises a forked hook having two tines separated by a notch that engages the shaft of the insertion tool as the tines engage the flanges of the trial spacer, to force the trial spacer into the enclosure. Alternatively and/or additionally, the same device may be utilized to remove the spacer from the enclosure, by reversing the position of the forked hook relative to the insertion tool and the spacer.

Figures 5A, 5B:
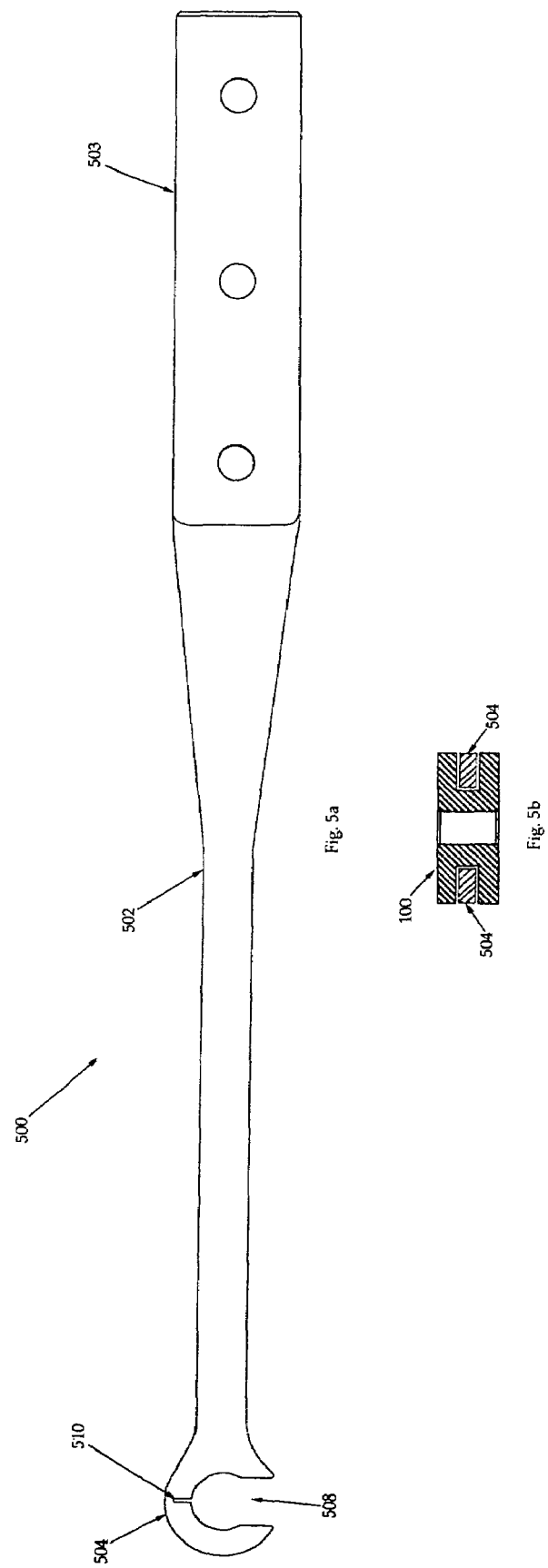
FIG. 5a illustrates a first embodiment of a spacer insertion tool 500 of the invention in a side view.
FIG. 5b is a cutaway view of the insertion tool of FIG. 5a holding the spacer of FIGS. 1a-c.

Referring now to FIG. 5a, a first embodiment of a spacer insertion tool 500 of the invention is illustrated in a side view. The insertion tool 500 includes an elongated shaft 502 and a handle 503 at one end of the shaft 502. At the other end of the shaft 502, the insertion tool 500 includes a semi-circular hook 504 that is adapted to hold an intervertebral spacer of the invention within an enclosure 506 of the hook 504. The central trunk of the spacer can be snapped into the enclosure 506 of the hook 504 so that the extent of the hook 504 fits loosely within the annular groove of the spacer and is flanked by the flanges of the spacer. The central trunk of the spacer can also be snapped out of the enclosure 506.

In this regard, the hook 504 has an opening 508 that temporarily expands when the central trunk of the spacer is forced through the opening 508. That is, the outer diameter of the central trunk is greater than the width of the opening 508, so that the central trunk cannot pass through the opening 508 without force. The application of a force sufficient to cause the opening 508 to expand when confronted with the central trunk causes the central trunk to pass through the opening 508. After the central trunk has cleared the opening 508, the opening 508 will contract. The temporary expansion in this embodiment is provided by the hook 504 being formed of a material having a low elasticity and the hook 504 being provided with a stress notch 510 on the extent (preferably located opposite the opening 508 for maximum efficiency) to ease the expansion.

Once the spacer is loaded into the enclosure, the opening 508, having contracted back to its resting width, prevents the central trunk from exiting the enclosure radially through the opening, because, as stated above, the outer diameter of the central trunk is greater than the width of the opening 508. Further, by flanking the extent of the hook 504, the flanges of the spacer prevent the spacer from exiting the enclosure laterally. The hook 504 therefore holds the spacer loosely in the enclosure so that the spacer can rotate about the cylindrical axis of the central trunk while being held by the hook 504.

Referring now to FIG. 5b, a cutaway view of the insertion tool 500 of FIG. 5a holding the spacer 100 of FIGS. 1a-c shows the extent of the hook 504 in cross-section and fitting within the annular groove of the spacer. It can be seen that to enable the spacer 100 to be loosely held in the enclosure, the width of the extent is smaller than the width of the annular groove, and the depth of the extent is less than the depth of the annular groove if it is desirable for the flanges to fully flank the extent. Preferably, as shown, the outer diameter of the hook 504 is substantially equal to the outer diameter of the spacer 100.

Referring now to FIG. 6a-b, an embodiment of a loading accessory 600 for a spacer insertion tool of the invention is illustrated in side and top views, respectively. The loading accessory 600 can be used to ease the passing of the central trunk of the spacer through the opening of the spacer insertion tool, both for loading the spacer into the enclosure and unloading the spacer from the enclosure. The loading accessory 600 includes an elongated shaft 602 and a forked hook 604 at an end of the shaft 602. A notch 606 having a base 608 separates the tines 610,612 of the forked hook 604.

The width of the notch 608 separating the tines 610,612 is wide enough to accommodate the width of the hook 504 of the insertion tool 500 and the width of the shaft 502 of the insertion tool 500, but narrow enough so that the tines 610,612 can engage the edges of the flanges of the spacer. Preferably, as shown, the curvature of the tines 608,610 follows the curvature of the edges of the flanges.

Referring now to FIG. 6c, the loading accessory 600 of FIGS. 6a-b is shown in operation to load the spacer 100 of FIG. 1a-c into the spacer insertion tool 500 of FIG. 5a. Initially, the spacer 100 is positioned adjacent the opening 508 of the insertion tool 500. Then, the tines 610,612 of the loading accessory 600 are passed on either side of the shaft 502 of the insertion tool 500 such that the notch 606 accommodates the shaft 502 and until the base 608 of the notch 606 contacts the shaft 502. Then, the loading accessory 600 is rotated, using the contact between the shaft 502 and the base 608 as a fulcrum, to cause the tines 610,612 to engage the flanges 104,106 of the spacer 100 and push them into the enclosure 506 of the tool 500. Applying a force to the rotation, sufficient to cause the opening 508 of the tool 500 to expand when confronted with the central trunk of the spacer, causes the central trunk to pass through the opening 508.

Referring now to FIG. 6*d*, the loading accessory 600 of FIGS. 6*a-b* is shown in operation to unload the spacer 100 of FIG. 1*a-c* from the spacer insertion tool 500 of FIG. 5*a*. Initially, with the spacer 100 held by the tool 500, the tines 610,612 of the loading accessory 600 are passed on either side of the shaft 502 of the insertion tool 500 such that the notch 606 accommodates the shaft 502 and until the base 608 of the notch 606 contacts the shaft 502. Then, the loading accessory 600 is rotated, using the contact between the shaft 502 and the base 608 as a fulcrum, to cause the tines 610,612 to engage the flanges 104,106 of the spacer 100 and push them out of the enclosure 506 of the tool 500. Applying a force to the rotation, sufficient to cause the opening 508 of the tool 500 to expand when confronted with the central trunk of the spacer, causes the central trunk to pass through the opening 508. The width of the notch 606 accommodates the width of the hook 504 as the spacer 100 is being pushed out of the enclosure 506.

The insertion tool of this embodiment, can be used to insert a series of constant thickness trial spacers (some of which may have beveled flange edges for easing the insertion between the collapsed bones and into the space to be distracted). More specifically, thinner trial spacers can initially be inserted into the spacer, followed successively by thicker trial spacers until the desired spacing is achieved. Once the appropriate spacing has been achieved, immobilization of the spine by fixation, fusion, or non-fusion techniques and devices, such as those set forth in co-pending U.S. patent application Ser. Nos. 09/906,117 and 09/906,118, entitled "An Intervertebral Spacer Device Having a Wave Washer Force Restoring Element" and "An Intervertebral Spacer Device Having a Spiral Wave Washer Force Restoring Element", respectively, as well as U.S. Pat. No. 5,989,291, entitled "An Intervertebral Spacer Device", each of which has been assigned to the same assignee as this present invention, the specifications of which are all fully incorporated herein by reference, may be desirable.

While simple distraction to a constant height across the intervertebral space is appropriate for standard disc compression pathologies, in the case of scoliosis, simple constant thickness distraction is insufficient to remediate the pathological condition. What is necessary is the distraction of the sequence of spaces, each to an appropriate angle and height, such that the overall spinal configuration is anatomically correct. Tapered trial spacers, such as those disclosed in the present application, are the first such distraction tools to provide such a tailored correction of the misangulation of the spinal bones.

More particularly, the surgeon inserts the tapered trial spacers into the intervertebral space (presumably from the anterior, or anterio-lateral, approach) with the narrow edge of the trial spacer forming a wedge and sliding between the adjacent bones. By utilizing either a second or third embodiment of the spacer insertion tool, described more fully hereinafter with respect to FIGS. 7*a-c* and 8*a-c* respectively, the surgeon may turn the spacer around its axis within the intervertebral space to find the most appropriate rotational position (corresponding to the most desirable straightening effect on the spinal column). Stated alternatively, each of the tapered trial spacers has an overall wedge shape that generally corresponds to the pathological tapering of the adjacent bones that characterizes scoliosis. By rotating the wedge-shaped spacer after it has been placed between the adjacent bones, the overall disc alignment may be compensated, restoring appropriate anatomical status. It should be understood that additional rotation of the spacer may restore lordosis to the spine, and that over-rotation (if the particular spine is flexible enough) of the spacer would result in a pathological curvature in the opposite direction.

Figure 3A:
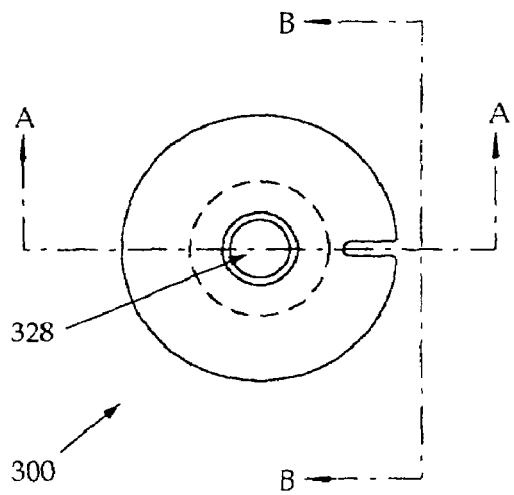
FIGS. 3a-c illustrate a third embodiment of an intervertebral spacer of the invention in side, top and side cutaway views, respectively.
Figure 3B:
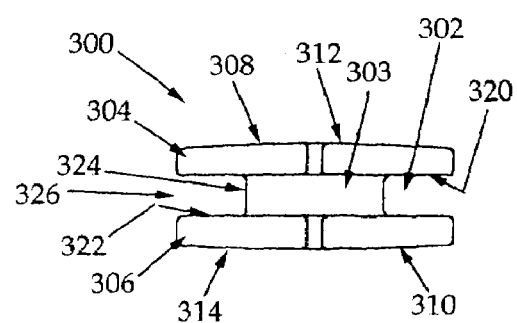
Figure 3C:
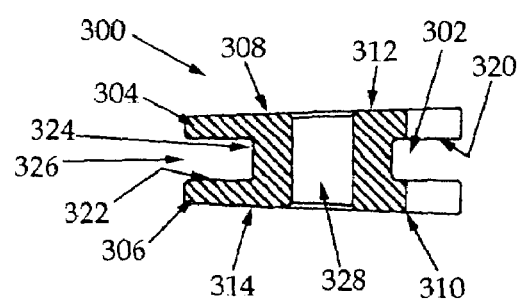

Referring now to FIGS. 3*a-c*, a third embodiment of an intervertebral spacer 300 of the invention is illustrated in side, top and side cutaway views, respectively. Similarly to the spacer 100, the spacer 300 is a cylindrical disc with an annular groove 302 that forms a central trunk 303 and radial flanges 304,306 at each end of the trunk 303. However, in this embodiment, support portions 308,310 of the top and bottom surfaces 312,314 of the disc are not parallel, providing an overall taper to the spacer 300 at an angle. Still, similarly to the spacer 100, the walls 320,322 of the annular groove 302 are parallel, such that the floor 324 of the groove 302 is as wide as the opening 326 of the groove 302. Further in this embodiment, the spacer 300 has a central bore 328.

Figure 3D:
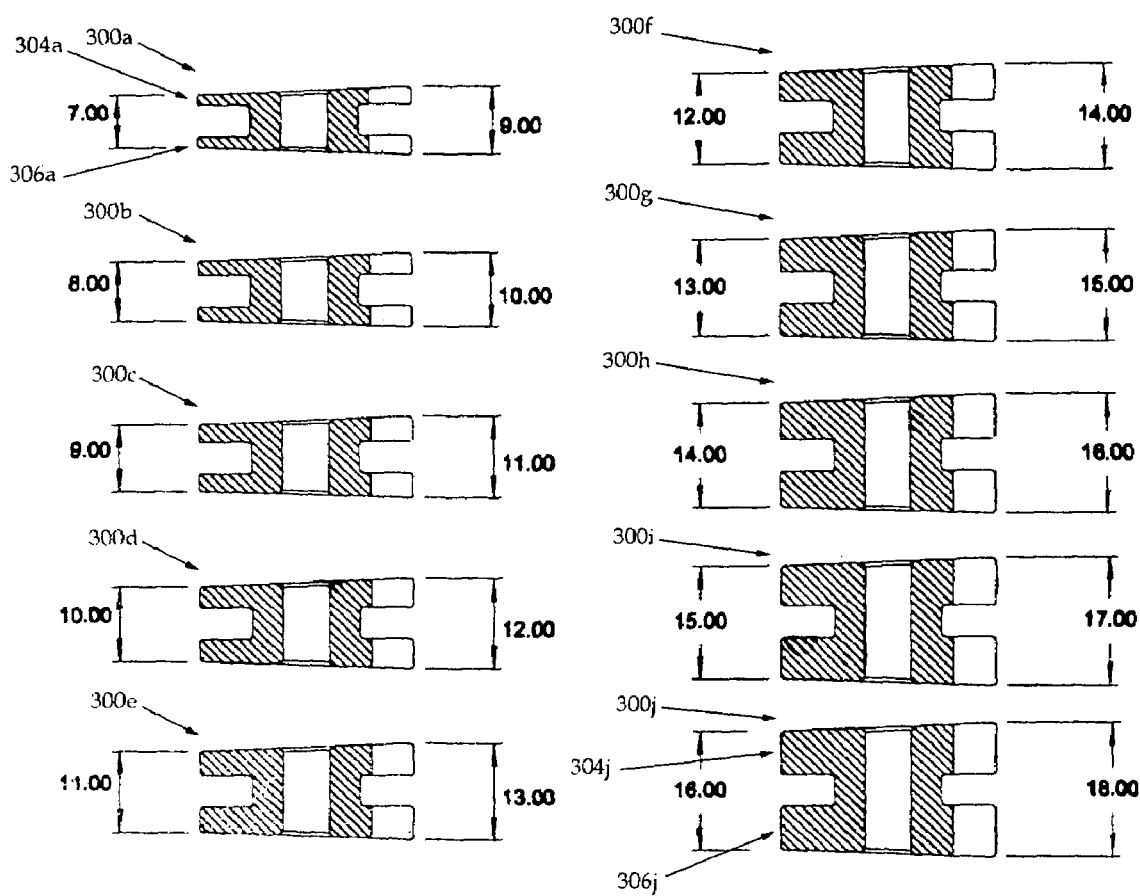
FIG. 3d illustrates a third set of tapered intervertebral spacers of the invention in a side view.

Referring now to FIG. 3*d*, a set of tapered intervertebral spacers 300*a-j* of the invention are illustrated in a side view. Each spacer 300*a-j* is formed generally similarly to the intervertebral spacer 300 of FIGS. 3*a-c*, except that each spacer 300*a-j* has a predetermined maximum depth (denoted by the preferred maximum depth dimension identified adjacent each spacer) and a predetermined minimum depth (denoted by the preferred minimum depth dimension identified adjacent each spacer), each provided in that while each spacer 300*a-j* shares the same annular groove width dimension as the other spacers, each spacer 300*a-j* has a different maximum flange thickness dimension and a different minimum flange thickness dimension. For example, the flanges 304*j*,306*j* have a thicker maximum flange thickness dimension and a thicker minimum flange thickness dimension than the flanges 304*a*,306*a*.

Figure 4A:
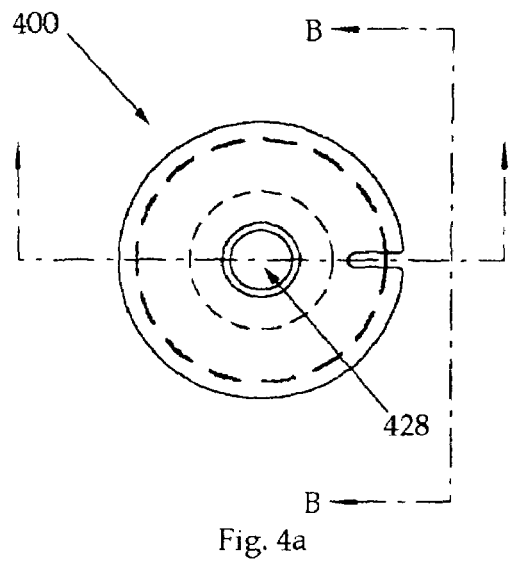
FIGS. 4a-c illustrate a fourth embodiment of an intervertebral spacer of the invention in side, top and side cutaway views, respectively.
Figure 4B:
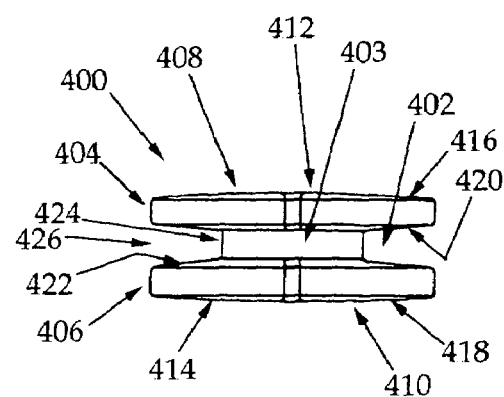
Figure 4C:
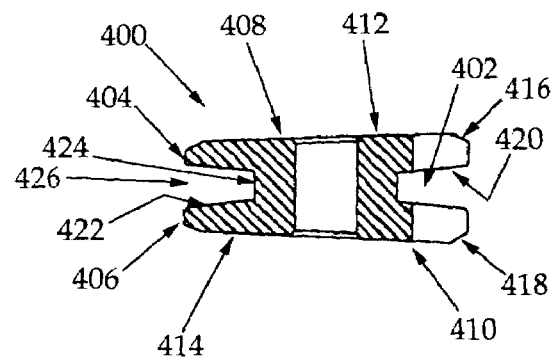

Referring now to FIGS. 4*a-c*, a fourth embodiment of an intervertebral spacer 400 of the invention is illustrated in side, top and side cutaway views, respectively. Similarly to the spacer 200, the spacer 400 is a cylindrical disc with an annular groove 402 that forms a central trunk 403 and radial flanges 404,406 at each end of the trunk 403. However, in this embodiment, support portions 408,410 of the top and bottom surfaces 412,414 of the disc are not parallel. Still, similarly to the spacer 200, the flanges 404,406 are radially tapered in that an outer edge 416 of the top surface 412 is tapered toward an outer edge 418 of the bottom surface 414. Further in this embodiment, similarly to the spacer 200, the walls 420,422 of the annular groove 402 are tapered toward one another with the increasing depth of the groove 402, such that the floor 424 of the groove 402 is more narrow than the opening 426 of the groove. Further in this embodiment, the spacer 400 has a central bore 428.

Figure 4D:
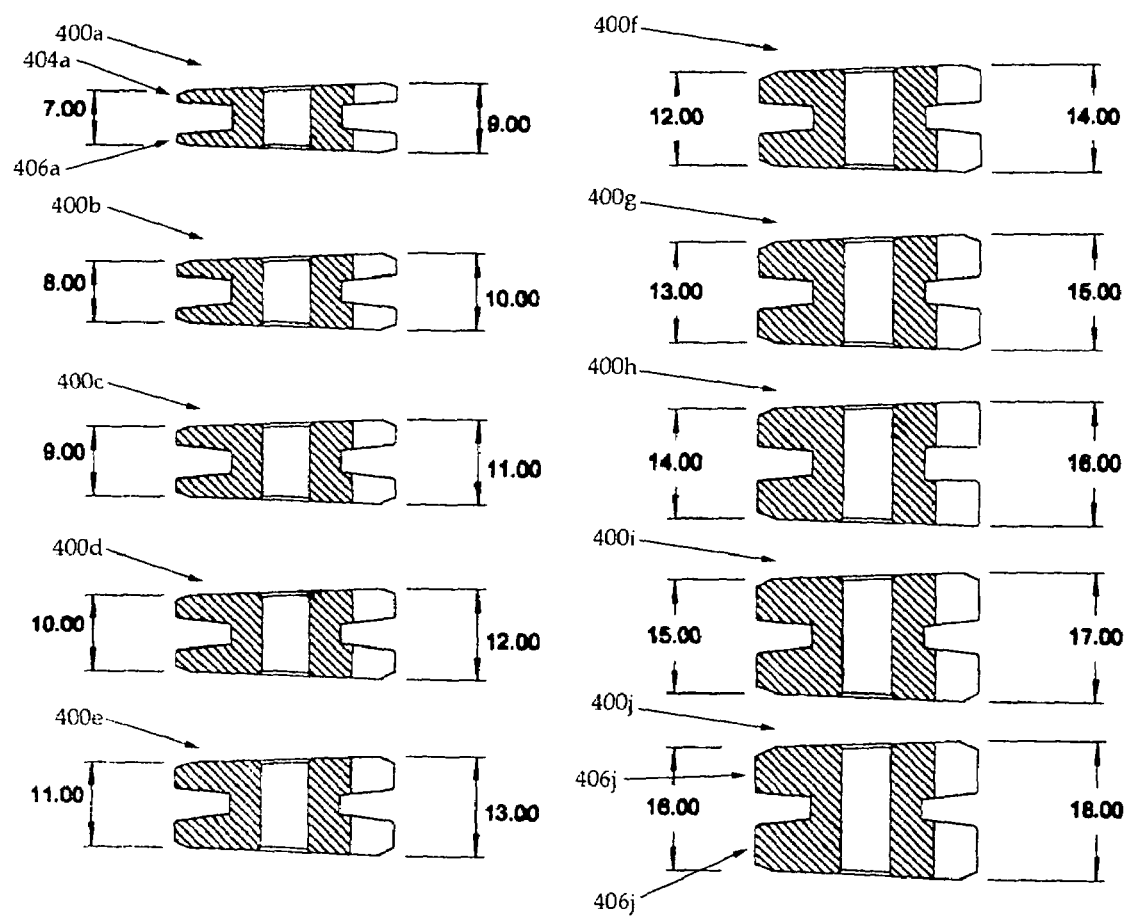
FIG. 4d illustrates a fourth set of tapered intervertebral spacers of the invention in a side view.

Referring now to FIG. 4*d*, a set of tapered intervertebral spacers 400*a-j* of the invention are illustrated in a side view. Each spacer 400*a-j* is formed generally similarly to the intervertebral spacer 400 of FIGS. 4*a-c*, except that each spacer 400*a-j* has a predetermined maximum depth (denoted by the preferred maximum depth dimension identified adjacent each spacer) and a predetermined minimum depth (denoted by the preferred minimum depth dimension identified adjacent each spacer), each provided in that while each spacer 400*a-j* shares the same annular groove width dimension as the other spacers, each spacer 400*a-j* has a different maximum flange thickness dimension and a different minimum flange thickness dimension. For example, the flanges 404j,406j have a thicker maximum flange thickness dimension and a thicker minimum flange thickness dimension than the flanges 404a,406a.

It should understood that the various features of the different embodiments of the intervertebral spacer of the invention discussed above can be used in various combinations and permutations to form the illustrated embodiments and other embodiments of the intervertebral spacer of the invention. In some embodiments, the walls of the annular groove are parallel. In other embodiments, they are not parallel. In some embodiments where they are not parallel, they are tapered toward one another with the increasing depth of the groove. In other embodiments where they are not parallel, they are tapered toward one another with the decreasing depth of the groove. In some embodiments, the support portions of the top and bottom surfaces are parallel. In other embodiments, they are not parallel. In some embodiments, the flanges are radially tapered in that the outer edge of the top surface is tapered toward an outer edge of the bottom surface. In other embodiments, the flanges are not radially tapered. In some embodiments, the spacer has a central bore. In other embodiments, the spacer does not have a central bore.

It should be understood that while in the illustrated embodiments where spacers in a set have an overall taper, the angle of the overall taper of each spacer in the set is the same as the angle of the overall taper of the other spacers in the set, the invention encompasses a set of spacers in which the angle of the overall taper of each spacer in the set is different than the angle of the overall taper of at least one other spacer in the set.

It should be understood that while in the illustrated embodiments where the spacer has an overall taper, the angle of the overall taper can be predetermined, such that the maximum flange thickness and the minimum flange thickness can be selected to achieve a desired overall taper angle.

It should be understood that while in the illustrated embodiments the spacers are shown as having a cylindrical shape, it should be understood that in other embodiment, the spacers can have oval, square, or rectangular cross-sections, or cross-sections of other shapes, provided that any corners are rounded as necessary to prevent damage to surrounding tissue.

As suggested previously, the insertion, rotation and removal of the tapered trial intervertebral spacers requires an alternate spacer insertion tool. This second embodiment of the spacer insertion tool includes a handle and an elongated dual shaft, the dual shaft culminating in a trial spacer grasping pincer, rather than the simple hook of the first embodiment. This pincer differs from the hook of the first embodiment of the trial spacer insertion tool described above, inasmuch as the dual shaft includes a fixed shaft and a selectively engagable shaft which, together, form pincer. More specifically, the fixed shaft includes a semicircular hook portion of the pincer at its distal end, having an enclosure within which a trial spacer can be placed. The selectively engagable shaft includes the complementary portion of the pincer, which moves toward the hook portion to grasp and hold the trial spacer when the engagable shaft is engaged, and moves away from the hook portion to release the trial spacer when the engagable shaft is disengaged. (The spacer can be unloaded and loaded when the engagable shaft is disengaged.) The engagement action prevents the spacer from moving relative to the tool, and therefore permits the surgeon to rotate the tapered spacer in between the vertebral bodies (by contrast, the first embodiment of the trial spacer insertion instrument permitted the spacer to rotate freely in the enclosure of the hook).

Figures 7A, 7B:
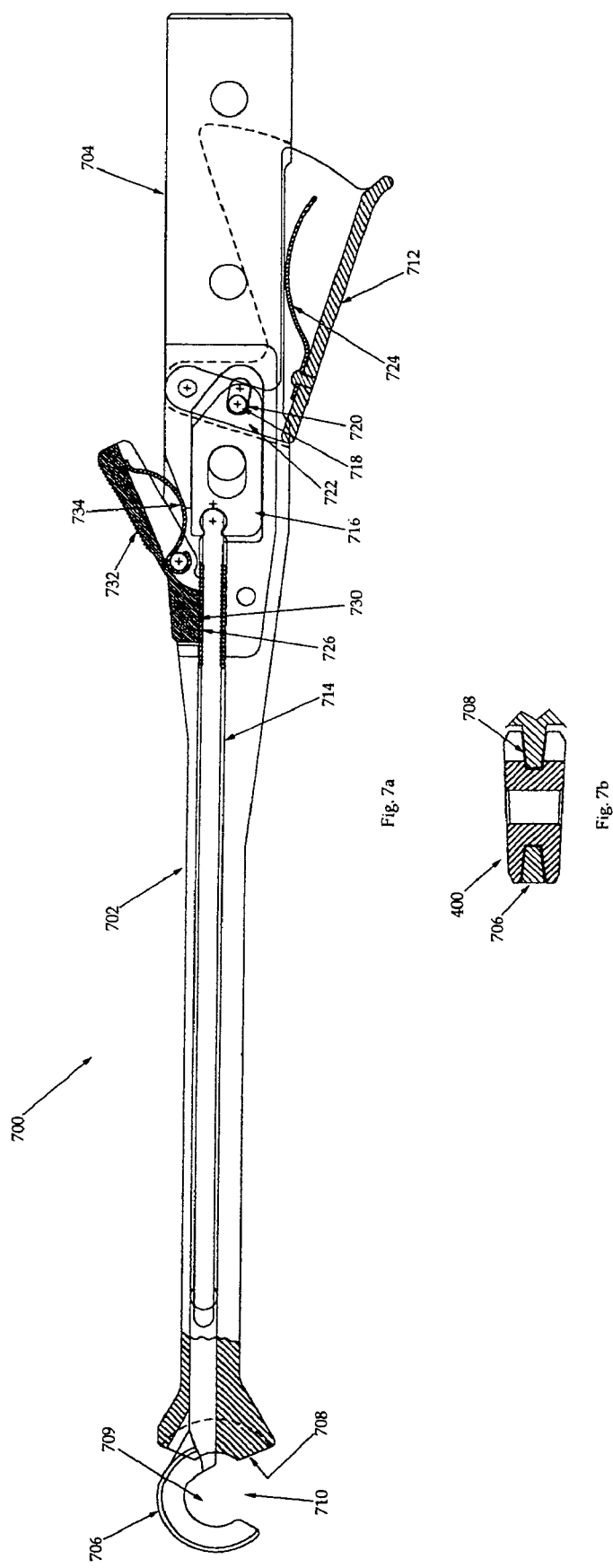
FIG. 7a illustrates another embodiment of a spacer insertion tool of the invention in a side view.
FIG. 7b is a cutaway view of the insertion tool of FIG. 7a holding the spacer of FIGS. 4a-c.

Referring now to FIG. 7a, another embodiment of a spacer insertion tool 700 of the invention is illustrated in a side view. The insertion tool 700 includes an elongated shaft 702 and a handle 704 at one end of the shaft 702. The insertion tool 700 further includes a compression assembly that is adapted to hold an intervertebral spacer of the invention at the other end of the shaft 702 so that the spacer cannot move when held. The insertion tool 700 further includes a release assembly that is adapted to release the spacer from being held.

The compression assembly includes a semicircular hook 706 at the other end of the shaft 702 and a compression surface 708 adjacent the hook 706. The hook 706 has an enclosure 709 defined by the extent of the hook 706 and an opening 710 through which the central trunk can pass freely to be placed into the enclosure 709. That is, the width of the opening 710 is greater than the diameter of the central trunk. When the central trunk is placed within the enclosure 709, the extent of the hook 706 fits loosely within the annular groove of the spacer.

The compression assembly further includes a compression trigger 712 mechanically connected to the hook 706 such that as the compression trigger 712 is placed in an engaged position, the hook 706 is pulled toward the compression surface 708. The mechanical connection includes a rod 714 connected at one end to the hook 706 and at the other end to a plate 716. A rod 718 protruding from the plate 716 is engaged by a slot 720 in a lever 722 attached to the compression trigger 712. When the compression trigger 712 is engaged, the rod 714 of the lever 722 pulls the plate 716 by the slot 720. The plate 716 in turn pulls the rod 714, which in turn pulls the hook 704 toward the compression surface 708.

When the hook 706 is pulled toward the compression surface 708 when the central trunk of the spacer is in the enclosure 709, the central trunk is compressed within the enclosure 709 between the hook 706 and the compression surface 708 so that the spacer cannot move.

The release assembly includes a spring 724 biasing the compression trigger 712 to a disengaged position. Therefore, after the compression trigger 712 is released, it moves to the disengaged position. However, so that the central trunk remains compressed within the enclosure even after the compression trigger 712 is released (e.g., so that the surgeon does not need to continue holding the compression trigger 712 to effect the compression), the compression assembly further includes teeth 726 on the rod 714 and corresponding teeth 730 that confront the rod teeth 726 to prevent the rod 714 from retreating, to maintain the compression.

The release assembly further includes a release trigger 732 that can be engaged to release the rod teeth 726 from the corresponding teeth 730 to allow the rod 714 to return to its rest position, thereby alleviating the compression. More specifically, the release trigger 732 has the corresponding teeth 730 and the release assembly further includes a spring 734 that biases the release trigger 732 toward a position in which the corresponding teeth 730 engage the rod teeth 726. This arrangement allows the release trigger 732 to be engaged by pressing the release trigger 732 with a force great enough to overcome the bias of the spring 734, so that the corresponding teeth 730 are disengaged from the rod teeth 726. Therefore, when the release trigger 732 is pressed, the compression is alleviated, and the central trunk of the spacer can be freely passed through the opening 710 to be taken out of the enclosure 709.

Referring now to FIG. 7b, a cutaway view of the insertion tool 700 of FIG. 7a holding the spacer 400 of FIGS. 4a-c shows the extent of the hook 706 in cross-section and fitting within the annular groove of the spacer as the spacer is compressed between the compression surface 708 and the hook 706. It can be seen that the width of the extent of the hook 706 is smaller than the width of the annular groove, and the depth of the extent is less than the depth of the annular groove if it is desirable for the flanges to fully flank the extent. Preferably, as shown, the outer diameter of the hook 706 is substantially equal to the outer diameter of the spacer 400.

Figure 8A:
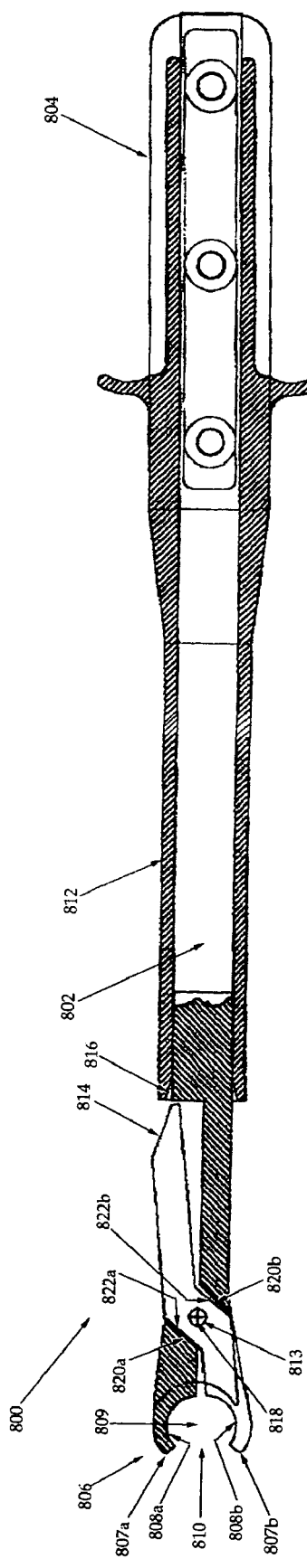
FIGS. 8a-b illustrates yet another embodiment of a spacer insertion tool of the invention in open and closed side views, respectively.
Figure 8B:
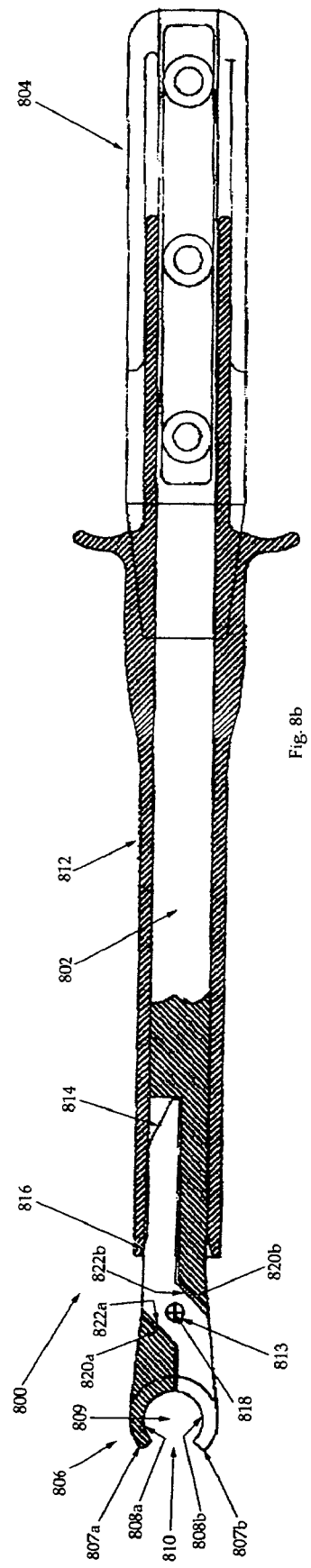

Referring now to FIGS. 8a-b, yet another embodiment of a spacer insertion tool 800 of the invention is illustrated in open and closed side views, respectively. The insertion tool 800 includes an elongated shaft 802 and a handle 804 at one end of the shaft 802. The insertion tool 800 further includes a compression assembly that is adapted to hold an intervertebral spacer of the invention at the other end of the shaft 802 so that the spacer cannot move when held. The insertion tool 800 further includes a release assembly that is adapted to release the spacer from being held.

The compression assembly includes a claw 806 at the other end of the shaft 802 having opposing pincers 807a, 807b, each providing one of opposing compression surfaces 808a, 808b. The claw 806 has an enclosure 809 defined by the extents of the pincers 807a, 807b and an opening 810 through which the central trunk can pass freely to be placed into the enclosure 809 when the claw 806 is open (i.e., when the opposing pincers 807a, 807b are separated). That is, the width of the opening 810 is greater than the diameter of the central trunk when the claw 806 is open. When the central trunk is placed within the enclosure 809, the extents of the pincers 807a, 807b fit loosely within the annular groove of the spacer.

The compression assembly further includes a compression slide 812 that when moved to an engaged position (here, a forward position shown in FIG. 8b) closes the claw 806. The closure of the claw 806 by the compression slide 812 is effected as follows. One of the pincers 807a is in a fixed position relative to the elongated shaft 802 whereas the other pincer 807b is adapted to rotate about an axis transverse to the shaft 802. In this embodiment, the rotation is provided by a pin 813 passing through each pincer at a rotation point along the transverse axis. One position of the movable pincer 807b along the rotation path (shown in FIG. 8a) defines the opened claw 806 in that the pincers 807a, 807b are separated. Another position of the movable pincer 807b along the rotation path (shown in FIG. 8b) defines the closed claw 806 in that the pincers 807a, 807b are brought together. When the pincers 807a, 807b are separated, an engagement surface 814 of the movable pincer 807b is placed in an available compression path of an engagement surface 816 of the compression slide 812. The engagement surface 814 is tapered so that when the compression slide 812 is moved to the engaged, the engagement surface 816 of the compression slide 812 moves along the available compression path and engages the tapered surface 814 to push the surface 814 aside and thereby cause a rotation of the movable pincer 807b to the position defining the closed claw 806.

When the pincers 807a, 807b are thereby brought together to close the claw 806 when the central trunk of the spacer is in the enclosure 809, the compression surfaces 808a, 808b come to bear on the central trunk to compress it within the enclosure 809 so that the spacer cannot move.

The release assembly includes a spring 818 biasing the movable pincer 807b to the rotation path position defining the open claw 806. Therefore, when the compression slide 812 is moved to a disengaged position (here, a backward position), the engagement surface 816 of the compression slide 812 moves along an available release path (here, a backtracking along the compression path) and frees the engagement surface 814 of the movable pincer 807b to allow the engagement surface 814 to return to a place in the available compression path by the biasing action of the spring 818. When the claw 806 is open, the compression is alleviated and the central trunk of the spacer can be freely passed through the opening 810 to be taken out of the enclosure 809.

The release assembly further includes at least one barrier 820a, 820b that limits the biasing action of the spring 818 by preventing the movable pincer 807b from rotating beyond the position that places the engagement surface 814 in the available compression path. In this embodiment, confrontation surfaces 822a, 822b on the movable pincer 807b confront the barriers 820a, 820b as the pincer 807b rotates toward the rotation path position defining the open claw 806 under the biasing force of the spring 818. When the engagement surface 814 is returned to the place in the available compression path, the barriers 820a, 820b prevent the confrontation surfaces 822a, 822b from advancing further. The spring 818 and the barriers 820a, 820b maintain the movable pincer 807b in this position until the compression slide 812 is advanced toward the engaged position by a force great enough to overcome the biasing force of the spring 818.

Figure 8C:
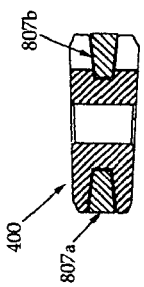
FIG. 8c is a cutaway view of the insertion tool of FIGS. 8a-b holding the spacer of FIGS. 4a-c.

Referring now to FIG. 8c, a cutaway view of the insertion tool 800 of FIGS. 8a-b holding the spacer 400 of FIGS. 4a-c shows the extents of the pincers 807a, 807b in cross-section and fitting within the annular groove of the spacer as the spacer is compressed between the compression surfaces 808a, 808b. It can be seen that the width of each extent is smaller than the width of the annular groove, and the depth of each extent is less than the depth of the annular groove if it is desirable for the flanges to fully flank the extents. Preferably, as shown, the outer diameter of the claw 806 is substantially equal to the outer diameter of the spacer 400.

There are alternative insertion and rotating instruments that may be designed, so long as they selectively and alternatingly release or hold the trial spacer securely against rotation (the spacer can't rotate freely if it is to be turned in the intervertebral space). The tapered trial spacers themselves can include angle markers that clearly indicate to the surgeon the amount of rotation that was necessary for the correction of the spinal deformity. Such angle markers can also serve as a guide for the implantation of a secondary bone graft (e.g., a femoral ring) or another intervertebral spacer device.

Once the surgeon has determined the appropriate geometry for the surgical implants via the trial spacers, he or she is ready to immobilize the spine in that position. While multiple ways for immobilizing the spine are disclosed in the prior art, any one of which may be suitable for the specific surgical patient's treatment, three alternative ways are herein described.

First, the trial spacers may be left in the patient while rod fixation apparatuses (anterior or posterior) are mounted to the spine, thereby holding the spine in its desired orientation even after the trial spacers are subsequently removed. Alternatively, surface plating and/or intervertebral cage devices may be mounted to the spine to promote fusion without the need for bulky rod assemblies. (While this approach may seem more surgically desirable, questions regarding the long-term stability of these constructs have led to some surgeons to choose combinations of rodding and cages.)

A third approach to immobilizing the corrected spine is to insert a shaped bone graft, or suitably contoured porous metal spacer, into the properly distracted intervertebral space, and either plating or using rod fixation to hold the construct stable as the spine fuses. The insertion of a femoral ring allograft, or porous metal implant, into an intervertebral space is described more fully in co-pending U.S. patent application Ser. Nos. 09/844,904 and 09/906,123, entitled "A Porous Interbody Fusion Device Having Integrated Polyaxial Locking Interference Screws" and "Porous Intervertebral Distraction Spacers", assigned to the same assignee as the present invention, the specifications of each being fully incorporated herein by reference.

The tapered trial spacers may also serve as precursors (measuring instruments) for another spacer (e.g., a porous metal spacer), similarly shaped, which is inserted into the intervertebral space by the same instrument.

The invention claimed is:

1. A trial spacer kit comprising:
   a plurality of trial spacers of varying heights; each said trial spacer comprising
      a disc having a top surface and a bottom surface, a distance between the top and bottom surfaces defining a height of said spacer,
      an annular groove formed in said disc that defines a central trunk of said spacer, the central trunk having an upper end and a lower end,
      a first radial flange provided at the upper end of the central trunk and a second radial flange provided at the lower end of the central trunk;
      the annular grooves of each of said trial spacers having a common dimension;
      the radial flanges of each of said spacers having a different thickness so that the height of each said spacer is different.

2. The trial spacer kit as claimed in claim 1, wherein each said disc is substantially cylindrical.

3. The trial spacer kit as claimed in claim 1, wherein each said spacer has a central bore extending between the top surface and the bottom surface of said disc.

4. The trial spacer kit as claimed in claim 3, wherein the central bore extends through the central trunk of each said spacer.

5. The trial spacer kit as claimed in claim 1, wherein the top and bottom surfaces of each said disc are parallel to one another.

6. The trial spacer kit as claimed in claim 1, wherein central sections of the top and bottom surfaces are parallel to one another.

7. The trial spacer kit as claimed in claim 6, wherein the central sections of the top and bottom surfaces of each said spacer are parallel and an outer edge of the top surface is tapered toward an outer edge of the bottom surface.

8. The trial spacer as claimed in claim 1, wherein the first radial flange has a first interior wall and the second radial flange has a second interior wall that faces the first interior wall, the first and second interior walls defining upper and lower limits of said annular groove.

9. The trial spacer kit as claimed in claim 8, wherein the first and second interior walls extend in directions that are parallel to one another.

10. The trial spacer kit as claimed in claim 9, wherein the first and second interior walls have sections that are parallel to one another.

11. The trial spacer kit as claimed in claim 8, wherein the first and second interior walls taper toward one another between outer edges of said radial flanges and the central trunk of said spacer.

12. The trial spacer kit as claimed in claim 1, wherein the top and bottom surfaces of each said spacer are substantially flat and non-parallel to one another so that each said spacer is tapered between a leading end and a trailing end thereof.

13. The trial spacer kit as claimed in claim 1, wherein an outer edge of said first radial flange and an outer edge of said second said radial flange are tapered toward one another.

14. The trial spacer kit as claimed in claim 13, wherein the interior walls that define said annular groove taper inwardly toward one another between the outer edges of said radial flanges and the central post, wherein said annular groove is narrower adjacent the central post and wider adjacent the outer edges of said radial flanges.

15. The trial spacer kit as claimed in claim 1, further comprising an instrument for holding each of said spacers during insertion and removal into and out from between adjacent vertebral bones, said instrument comprising a shaft having a distal end and a spacer holding structure formed at the distal end, said spacer holding structure being adapted to hold said spacers at the annular grooves thereof.

16. The trial spacer kit as claimed in claim 15, wherein said instrument has a longitudinal axis extending along the shaft thereof, said spacer holding structure having an opening for receiving the central trunks of said spacers.

17. The trial spacer kit as claimed in claim 16, wherein the opening of said spacer holding structure faces a direction that is substantially perpendicular to the longitudinal axis of said instrument.

18. The trial spacer kit as claimed in claim 15, further comprising a loading tool that facilitates loading and unloading of said spacers into and out of said holding instrument.

19. The trial spacer kit as claimed in claim 18, wherein said loading tool comprises a handle and a bifurcated end, said bifurcated end including a pair of similarly curved tines adapted for engaging said spacers as forces are applied to said spacers.

20. The trial spacer kit as claimed in claim 19, wherein said holding instrument and said loading tool engage one another at a fulcrum point.

21. The trial spacer kit as claimed in claim 1, wherein said spacer holding structure includes a hook adapted to hold said spacers at the annular grooves thereof, and wherein said hook has a semi-circular surface that conforms to the annular grooves formed in said discs.

22. The trial spacer kit as claimed in claim 1, wherein said hook is expandable.

23. The trial spacer kit as claimed in claim 22, wherein said hook includes a notch that enables an opening of said hook to expand and contract.

24. A trial spacer kit comprising:
   a plurality of trial spacers of varying heights; each said trial spacer comprising
      a disc having a top surface and a bottom surface, a distance between the top and bottom surfaces defining a height of said spacer,
      an annular groove formed in said disc that defines a central trunk of said spacer, the central trunk having an upper end and a lower end,
      a first radial flange provided at the upper end of the central trunk and a second radial flange provided at the lower end of the central trunk;
      the annular grooves of each of said trial spacers having a common dimension;
      the radial flanges of each of said spacers having a different thickness so that the height of each said spacer is different; and
      an instrument for holding each of said spacers during insertion and removal into and out from between adjacent vertebral bones, said holding instrument including a hook adapted for holding said spacers at the annular grooves thereof.

25. A trial spacer kit comprising:

a plurality of trial spacers of varying heights; each said trial spacer comprising a disc having a top surface and a bottom surface, a distance between the top and bottom surfaces defining a height of said spacer, an annular groove formed in said disc that defines a central trunk of said spacer, the central trunk having an upper end and a lower end, a first radial flange provided at the upper end of the central trunk and a second radial flange provided at the lower end of the central trunk;

the annular grooves of each of said trial spacers having a common dimension;

the radial flanges of each of said spacers having a different thickness so that the height of each said spacer is different;

a holding instrument including a hook adapted for holding said spacers at the annular grooves thereof; and a loading tool for loading and unloading said spacers into and out of said holding instrument.

* * * * *